United States Patent
Siqueira et al.

(10) Patent No.: US 9,011,625 B2
(45) Date of Patent: *Apr. 21, 2015

(54) NONWOVEN COMPOSITE CONTAINING AN APERTURED ELASTIC FILM

(71) Applicant: Kimberly-Clark Worldwide, Inc., Neenah, WI (US)

(72) Inventors: Jose Siqueira, Roswell, GA (US); Ann L. McCormack, Cumming, GA (US); Norman Brown, Roswell, GA (US); Wing-Chak Ng, Suwanee, GA (US); Howard M. Welch, Woodstock, GA (US); Margaret G. Latimer, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/733,987

(22) Filed: Jan. 4, 2013

(65) Prior Publication Data

US 2013/0126070 A1 May 23, 2013

Related U.S. Application Data

(60) Continuation of application No. 12/029,082, filed on Feb. 11, 2008, now Pat. No. 8,361,913, which is a division of application No. 11/513,497, filed on Aug. 31, 2006, now Pat. No. 7,803,244.

(51) Int. Cl.
*B32B 38/04* (2006.01)
*B32B 3/10* (2006.01)
(Continued)

(52) U.S. Cl.
CPC .............. *B32B 37/24* (2013.01); *A61F 13/4902* (2013.01); *B32B 3/266* (2013.01);
(Continued)

(58) Field of Classification Search
None
See application file for complete search history.

(56) References Cited

U.S. PATENT DOCUMENTS

| 3,338,992 A | 8/1967 | Kinney |
| 3,341,394 A | 9/1967 | Kinney |

(Continued)

FOREIGN PATENT DOCUMENTS

| WO | WO 9516425 A1 | 6/1995 |
| WO | WO 9533390 A1 | 12/1995 |

(Continued)

OTHER PUBLICATIONS

Abstract of Japanese Patent No. JP2007084954, dated Apr. 5, 2007.

(Continued)

*Primary Examiner* — Barbara J Musser
(74) *Attorney, Agent, or Firm* — Dority & Manning, P.A.

(57) ABSTRACT

An elastic nonwoven composite that contains an elastic film laminated to one or more nonwoven web materials is provided. The composite is formed by passing the film through a nip to bond the film to the nonwoven web material(s). Concurrent with bond formation, apertures are also formed in the elastic film. The apertures are of a size sufficient to provide a desired level of texture, softness, hand feel, and/or aesthetic appeal to the composite without having a significant adverse effect on its elastic properties. Aperture and bond formation are accomplished in the present invention by selectively controlling certain parameters of the lamination process, such as film content, bonding pattern, degree of film tension, bonding conditions, etc.

28 Claims, 13 Drawing Sheets

(51) Int. Cl.
  *B32B 37/24* (2006.01)
  *A61F 13/49* (2006.01)
  *B32B 3/26* (2006.01)
  *B32B 5/26* (2006.01)
  *B32B 27/02* (2006.01)
  *B32B 27/08* (2006.01)
  *B32B 27/12* (2006.01)
  *B32B 27/20* (2006.01)
  *B32B 27/32* (2006.01)
  *B32B 37/14* (2006.01)
  *D04H 13/00* (2006.01)
  *B32B 37/00* (2006.01)
  *B32B 38/00* (2006.01)

(52) U.S. Cl.
  CPC ............ *B32B 5/26* (2013.01); *B32B 27/02* (2013.01); *B32B 27/08* (2013.01); *B32B 27/12* (2013.01); *B32B 27/20* (2013.01); *B32B 27/32* (2013.01); *B32B 37/0076* (2013.01); *B32B 37/144* (2013.01); *B32B 38/04* (2013.01); *B32B 2038/0028* (2013.01); *B32B 2038/047* (2013.01); *B32B 2305/20* (2013.01); *B32B 2307/51* (2013.01); *D04H 13/007* (2013.01)

(56) References Cited

U.S. PATENT DOCUMENTS

| | | |
|---|---|---|
| 3,354,506 A | 11/1967 | Raley |
| 3,494,821 A | 2/1970 | Evans |
| 3,502,538 A | 3/1970 | Petersen |
| 3,502,763 A | 3/1970 | Hartmann |
| 3,542,615 A | 11/1970 | Dobo et al. |
| 3,650,649 A | 3/1972 | Schippers |
| 3,692,618 A | 9/1972 | Dorschner et al. |
| 3,801,429 A | 4/1974 | Schrenk et al. |
| 3,802,817 A | 4/1974 | Matsuki et al. |
| 3,844,869 A | 10/1974 | Rust, Jr. |
| 3,849,241 A | 11/1974 | Butin et al. |
| 3,855,046 A | 12/1974 | Hansen et al. |
| 3,939,033 A | 2/1976 | Grgach et al. |
| 3,985,599 A | 10/1976 | Lepoutre et al. |
| 4,041,203 A | 8/1977 | Brock et al. |
| 4,144,370 A | 3/1979 | Boulton |
| 4,259,399 A | 3/1981 | Hill |
| 4,323,534 A | 4/1982 | DesMarais |
| 4,340,563 A | 7/1982 | Appel et al. |
| 4,374,888 A | 2/1983 | Bornslaeger |
| 4,663,220 A | 5/1987 | Wisneski et al. |
| 4,704,116 A | 11/1987 | Enloe |
| 4,704,238 A | 11/1987 | Okuyama et al. |
| 4,720,415 A | 1/1988 | Vander Wielen et al. |
| 4,726,976 A | 2/1988 | Karami et al. |
| 4,766,029 A | 8/1988 | Brock et al. |
| 4,781,966 A | 11/1988 | Taylor |
| 4,789,592 A | 12/1988 | Taniguchi et al. |
| 4,795,668 A | 1/1989 | Krueger et al. |
| 4,834,738 A | 5/1989 | Kielpikowski et al. |
| 4,886,512 A | 12/1989 | Damico et al. |
| 4,937,299 A | 6/1990 | Ewen et al. |
| 4,965,122 A | 10/1990 | Morman |
| 4,981,747 A | 1/1991 | Morman |
| 4,981,750 A | 1/1991 | Murphy et al. |
| 5,043,036 A | 8/1991 | Swenson |
| 5,057,368 A | 10/1991 | Largman et al. |
| 5,069,970 A | 12/1991 | Largman et al. |
| 5,093,422 A | 3/1992 | Himes |
| 5,096,532 A | 3/1992 | Neuwirth et al. |
| 5,108,820 A | 4/1992 | Kaneko et al. |
| 5,110,403 A | 5/1992 | Ehlert |
| 5,162,074 A | 11/1992 | Hills |
| 5,169,706 A | 12/1992 | Collier, IV et al. |
| 5,192,606 A | 3/1993 | Proxmire et al. |
| 5,207,962 A | 5/1993 | Hovis et al. |
| 5,213,881 A | 5/1993 | Timmons et al. |
| 5,218,071 A | 6/1993 | Tsutsui et al. |
| 5,226,992 A | 7/1993 | Morman |
| 5,272,236 A | 12/1993 | Lai et al. |
| 5,277,976 A | 1/1994 | Hogle et al. |
| 5,278,272 A | 1/1994 | Lai et al. |
| 5,284,703 A | 2/1994 | Everhart et al. |
| 5,304,599 A | 4/1994 | Himes |
| 5,322,728 A | 6/1994 | Davey et al. |
| 5,332,613 A | 7/1994 | Taylor et al. |
| 5,336,545 A | 8/1994 | Morman |
| 5,336,552 A | 8/1994 | Strack et al. |
| 5,382,400 A | 1/1995 | Pike et al. |
| 5,397,842 A | 3/1995 | Hamilton et al. |
| 5,399,219 A | 3/1995 | Roessler et al. |
| 5,464,688 A | 11/1995 | Timmons et al. |
| 5,466,410 A | 11/1995 | Hills |
| 5,472,775 A | 12/1995 | Obijeski et al. |
| 5,486,166 A | 1/1996 | Bishop et al. |
| 5,490,846 A | 2/1996 | Ellis et al. |
| 5,539,056 A | 7/1996 | Yang et al. |
| 5,540,796 A | 7/1996 | Fries |
| 5,558,659 A | 9/1996 | Sherrod et al. |
| 5,560,793 A | 10/1996 | Ruscher et al. |
| 5,567,501 A | 10/1996 | Srinivasan et al. |
| D375,844 S | 11/1996 | Edwards et al. |
| 5,571,619 A | 11/1996 | McAlpin et al. |
| 5,573,719 A | 11/1996 | Fitting |
| 5,595,618 A | 1/1997 | Fries et al. |
| 5,596,052 A | 1/1997 | Resconi et al. |
| 5,620,779 A | 4/1997 | Levy et al. |
| 5,649,916 A | 7/1997 | DiPalma et al. |
| 5,656,119 A | 8/1997 | Srinivasan et al. |
| 5,674,211 A | 10/1997 | Ekdahl |
| 5,702,377 A | 12/1997 | Collier, IV et al. |
| D390,708 S | 2/1998 | Brown |
| 5,714,107 A | 2/1998 | Levy et al. |
| 5,733,628 A | 3/1998 | Pelkie |
| 5,817,199 A | 10/1998 | Brennecke et al. |
| 5,830,555 A | 11/1998 | Srinivasan et al. |
| 5,851,935 A | 12/1998 | Srinivasan et al. |
| 5,931,823 A | 8/1999 | Stokes et al. |
| 5,932,497 A | 8/1999 | Morman et al. |
| 5,962,112 A | 10/1999 | Haynes et al. |
| 5,964,742 A | 10/1999 | McCormack et al. |
| 5,997,981 A | 12/1999 | McCormack et al. |
| 6,015,764 A | 1/2000 | McCormack et al. |
| 6,025,049 A | 2/2000 | Ouellette et al. |
| 6,025,050 A | 2/2000 | Srinivasan et al. |
| 6,060,638 A | 5/2000 | Paul et al. |
| D428,267 S | 7/2000 | Romano, III et al. |
| 6,090,325 A | 7/2000 | Wheat et al. |
| 6,093,665 A | 7/2000 | Sayovitz et al. |
| 6,106,925 A | 8/2000 | Palumbo |
| 6,110,158 A | 8/2000 | Kielpikowski |
| 6,111,163 A | 8/2000 | McCormack et al. |
| 6,150,002 A | 11/2000 | Varona |
| 6,200,669 B1 | 3/2001 | Marmon et al. |
| 6,231,948 B1 | 5/2001 | Ouellette et al. |
| 6,303,208 B1 | 10/2001 | Pelkie |
| 6,315,864 B2 | 11/2001 | Anderson et al. |
| 6,461,457 B1 | 10/2002 | Taylor et al. |
| 6,461,716 B1 | 10/2002 | Lee et al. |
| 6,500,563 B1 | 12/2002 | Datta et al. |
| 6,503,598 B1 | 1/2003 | Goda et al. |
| 6,511,465 B1 | 1/2003 | Freiburger et al. |
| 6,537,930 B1 | 3/2003 | Middlesworth et al. |
| 6,663,611 B2 | 12/2003 | Blaney et al. |
| 6,720,279 B2 | 4/2004 | Cree et al. |
| 6,808,789 B2 | 10/2004 | Pelkie et al. |
| 6,830,800 B2 | 12/2004 | Curro et al. |
| 6,849,319 B2 | 2/2005 | Cree et al. |
| 6,884,494 B1 | 4/2005 | Curro et al. |
| 6,888,044 B2 | 5/2005 | Fell et al. |
| 6,986,932 B2 | 1/2006 | Zink et al. |
| 7,008,496 B2 | 3/2006 | Morman |
| 7,037,569 B2 | 5/2006 | Curro et al. |
| 7,087,287 B2 | 8/2006 | Curro et al. |
| 7,141,132 B2 | 11/2006 | Shimakawa et al. |

(56) References Cited

U.S. PATENT DOCUMENTS

| | | |
|---|---|---|
| 7,208,217 B2 | 4/2007 | Deep et al. |
| 7,507,680 B2 | 3/2009 | Middlesworth et al. |
| 2002/0034912 A1 | 3/2002 | Curro et al. |
| 2003/0028165 A1 | 2/2003 | Curro et al. |
| 2003/0068951 A1 | 4/2003 | Boggs et al. |
| 2004/0060112 A1 | 4/2004 | Fell et al. |
| 2004/0102750 A1 | 5/2004 | Jameson |
| 2004/0110442 A1 | 6/2004 | Rhim et al. |
| 2004/0121687 A1 | 6/2004 | Morman et al. |
| 2004/0122396 A1 | 6/2004 | Maldonado et al. |
| 2005/0054255 A1 | 3/2005 | Morman et al. |
| 2005/0059941 A1 | 3/2005 | Baldwin et al. |
| 2005/0095943 A1 | 5/2005 | Griffin et al. |
| 2005/0158513 A1 | 7/2005 | Peacock et al. |
| 2005/0245162 A1 | 11/2005 | McCormack et al. |
| 2006/0148358 A1 | 7/2006 | Hall et al. |
| 2006/0151914 A1 | 7/2006 | Gerndt et al. |
| 2007/0141941 A1 | 6/2007 | DeLucia et al. |

FOREIGN PATENT DOCUMENTS

| | | |
|---|---|---|
| WO | WO 9829504 A1 | 7/1998 |
| WO | WO 9914047 A1 | 3/1999 |
| WO | WO 0056522 A1 | 9/2000 |
| WO | WO 0145616 A1 | 6/2001 |
| WO | WO 0187592 A1 | 11/2001 |
| WO | WO 2004060664 A1 | 7/2004 |
| WO | WO 2004060666 A1 | 7/2004 |
| WO | WO 2004060669 A1 | 7/2004 |
| WO | WO 2006024394 A1 | 3/2006 |
| WO | WO 2006071306 A1 | 7/2006 |

OTHER PUBLICATIONS

ASTM 1505-03 Density of Plastics by the Density-Gradient Technique.

ASTM 1525-07 Vicat Softening Temperature of Plastics.

ASTM D3418-03 Transition Temperatures and Enthalpies of Fusion and Crystallization of Polymers by Differential Scanning Calorimetry.

Russell, S.J. (2003) Handbook of Nonwovens (Chapter 6—Thermal Bonding). The Textile Institute: Cambridge, pp. 1-11.

Handbook of Nonwovens—Chapter 6, Thermal Bonding, 2003, pp. 1-11.

Thermal Bonding—CompleteTextile Glossary, from Celanese Acetate LLC, 2001, 3 pages.

NONWOVEN COMPOSITE CONTAINING AN APERTURED ELASTIC FILM

RELATED APPLICATIONS

The present application is a continuation of U.S. application Ser. No. 12/029,082, filed on Feb. 11, 2008, now U.S. Pat. No. 8,361,913, which is a divisional of U.S. application Ser. No. 11/513,497, filed on Aug. 31, 2006, now U.S. Pat. No. 7,803,244, which are incorporated herein in their entirety by reference thereto.

BACKGROUND OF THE INVENTION

Elastic composites are commonly incorporated into products (e.g., diapers, training pants, garments, etc.) to improve their ability to better fit the contours of the body. For example, the elastic composite may be formed from an elastic film and one or more nonwoven web materials. The nonwoven web material may be joined to the elastic film while the film is in a stretched condition so that the nonwoven web material can gather between the locations where it is bonded to the film when it is relaxed. The resulting elastic composite is stretchable to the extent that the nonwoven web material gathered between the bond locations allows the elastic film to elongate. Unfortunately, elastic films often have unpleasant tactile aesthetic properties, such as feeling rubbery or tacky to the touch, making them unpleasant and uncomfortable against the wearer's skin. In an effort to improve these properties, attempts have been made to aperture the composite. For example, U.S. Pat. No. 6,830,800 to Curro, et al. describes a method in which an elastic material is joined between two webs. The elastic material is apertured in regions coincident the bond sites so that the first and second webs are joined through the apertures. Despite the benefits achieved, however, a need for improvement nevertheless remains.

SUMMARY OF THE INVENTION

In accordance with one embodiment of the present invention, a method of forming a nonwoven composite is disclosed. The method comprises forming an elastic film from a polymer composition and passing the film and a nonwoven web material through a nip formed by at least one patterned roll. At the nip, the film and the nonwoven web material are melt fused and the film is concurrently formed with apertures without substantially softening the polymer of the nonwoven web material. At least one of the apertures has a length of from about 200 to about 5000 micrometers. Further, the film is under tension at a stretch ratio of about 1.5 or more in the machine direction at the nip.

In accordance with another embodiment of the present invention, a nonwoven composite is disclosed that comprises an elastic film positioned adjacent and melt fused to a nonwoven web material at a plurality of discrete bond sites. The elastic film defines a plurality of apertures having a perimeter about which the discrete bond sites are proximately located. At least one of the apertures has a length of from about 200 to about 5000 micrometers.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
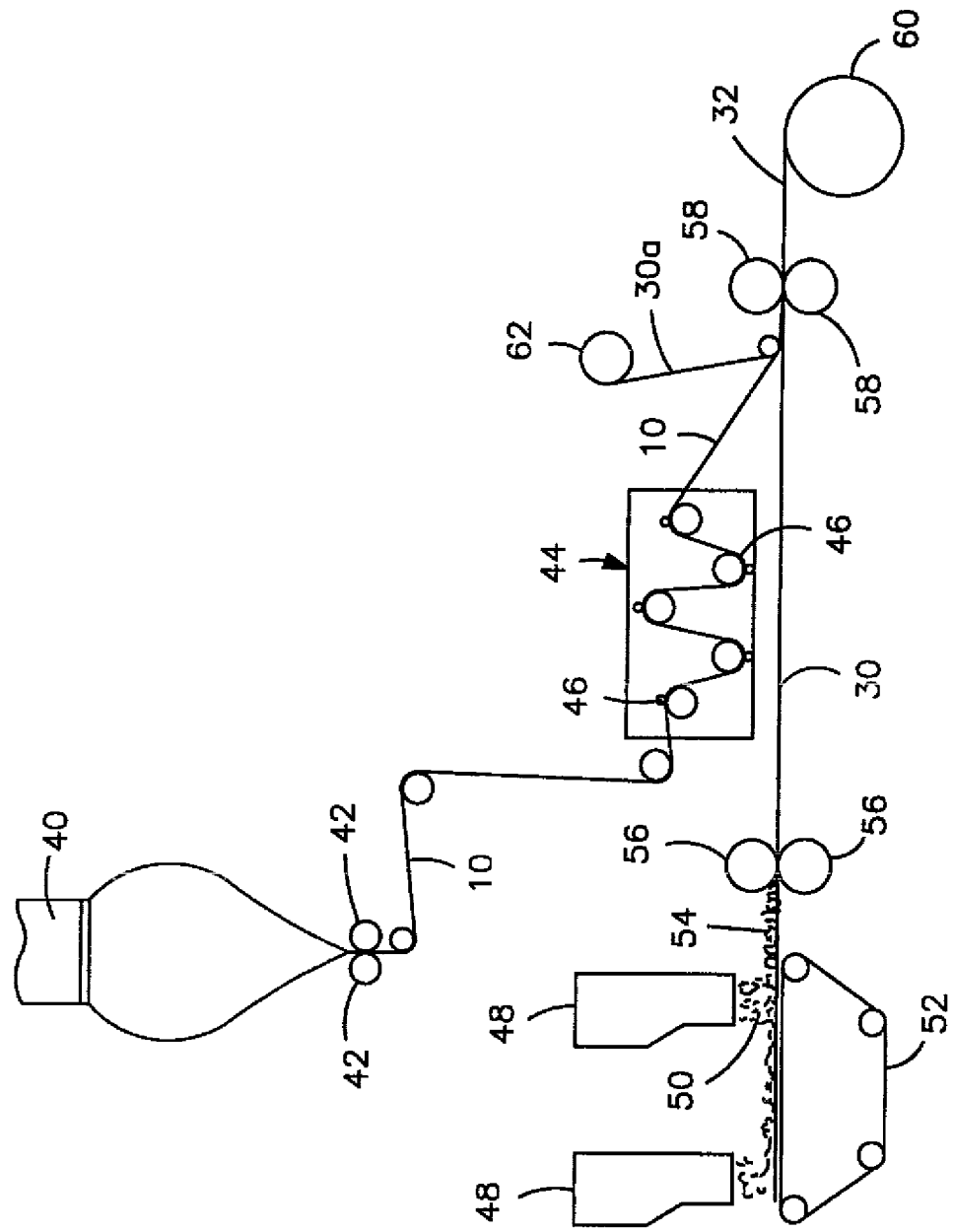
FIG. 1 schematically illustrates a method for forming a composite according to one embodiment of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein the term "nonwoven web" generally refers to a web having a structure of individual fibers or threads which are interlaid, but not in an identifiable manner as in a knitted fabric. Examples of suitable nonwoven fabrics or webs include, but are not limited to, meltblown webs, spunbond webs, bonded carded webs, airlaid webs, coform webs, hydraulically entangled webs, and so forth.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

As used herein, the terms "machine direction" or "MD" generally refers to the direction in which a material is produced. The term "cross-machine direction" or "CD" refers to the direction perpendicular to the machine direction.

As used herein the terms "extensible" or "extensibility" generally refers to a material that stretches or extends in the direction of an applied force by at least about 25%, in some embodiments about 50%, and in some embodiments, at least about 75% of its relaxed length or width. An extensible material does not necessarily have recovery properties. For example, an elastomeric material is an extensible material having recovery properties. A meltblown web may be extensible, but not have recovery properties, and thus, be an extensible, non-elastic material.

As used herein, the term "elastomeric" and "elastic" and refers to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of not more than 1.25 inches. Desirably, the material contracts or recovers at least 50%, and even more desirably, at least 80% of the stretched length.

As used herein, the terms "necked" and "necked material" generally refer to any material that has been drawn in at least one dimension (e.g., machine direction) to reduce its transverse dimension (e.g., cross-machine direction) so that when the drawing force is removed, the material may be pulled back to its original width. The necked material generally has a higher basis weight per unit area than the un-necked material. When the necked material is pulled back to its original width, it should have about the same basis weight as the un-necked material. This differs from the orientation of a film in which the film is thinned and the basis weight is reduced. The necking method typically involves unwinding a material from a supply roll and passing it through a brake nip roll assembly driven at a given linear speed. A take-up roll or nip, operating at a linear speed higher than the brake nip roll, draws the material and generates the tension needed to elongate and neck the material.

As used herein, the term "thermal point bonding" generally refers to a process performed, for example, by passing a material between a patterned roll (e.g., calender roll) and another roll (e.g., anvil roll), which may or may not be patterned. One or both of the rolls are typically heated.

As used herein, the term "ultrasonic bonding" generally refers to a process performed, for example, by passing a material between a sonic horn and a patterned roll (e.g., anvil roll). For instance, ultrasonic bonding through the use of a stationary horn and a rotating patterned anvil roll is described in U.S. Pat. No. 3,939,033 to Grgach, et al., U.S. Pat. No. 3,844,869 to Rust Jr., and U.S. Pat. No. 4,259,399 to Hill, which are incorporated herein in their entirety by reference thereto for all purposes. Moreover, ultrasonic bonding through the use of a rotary horn with a rotating patterned anvil roll is described in U.S. Pat. No. 5,096,532 to Neuwirth, et al., U.S. Pat. No. 5,110,403 to Ehlert, and U.S. Pat. No. 5,817,199 to Brennecke, et al., which are incorporated herein in their entirety by reference thereto for all purposes. Of course, any other ultrasonic bonding technique may also be used in the present invention.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a nonwoven composite that contains an elastic film laminated to one or more nonwoven web materials. The composite is formed by passing the film through a nip to bond the film to the nonwoven web material(s). Concurrent with bond formation, apertures are also formed in the elastic film. The apertures are of a size sufficient to provide a desired level of texture, softness, hand feel, and/or aesthetic appeal to the composite without having a significant adverse effect on its elastic properties. Aperture and bond formation are accomplished in the present invention by selectively controlling certain parameters of the lamination process, such as film content, bonding pattern, degree of film tension, bonding conditions, etc. In this regard, various embodiments of the present invention will now be described in more detail.

I. Elastic Film

The elastic film of the present invention is formed from one or more elastomeric polymers that are melt-processable, i.e. thermoplastic. Any of a variety of thermoplastic elastomeric polymers may generally be employed in the present invention, such as elastomeric polyesters, elastomeric polyurethanes, elastomeric polyamides, elastomeric copolymers, elastomeric polyolefins, and so forth. In one particular embodiment, elastomeric semi-crystalline polyolefins are employed due to their unique combination of mechanical and elastomeric properties. That is, the mechanical properties of such semi-crystalline polyolefins allows for the formation of films that readily aperture during thermal bonding, but yet retain their elasticity.

Semi-crystalline polyolefins have or are capable of exhibiting a substantially regular structure. For example, semi-crystalline polyolefins may be substantially amorphous in their undeformed state, but form crystalline domains upon stretching. The degree of crystallinity of the olefin polymer may be from about 3% to about 30%, in some embodiments from about 5% to about 25%, and in some embodiments, from about 5% and about 15%. Likewise, the semi-crystalline polyolefin may have a latent heat of fusion ($\Delta H_f$), which is another indicator of the degree of crystallinity, of from about 15 to about 75 Joules per gram ("J/g"), in some embodiments from about 20 to about 65 J/g, and in some embodiments, from 25 to about 50 J/g. The semi-crystalline polyolefin may also have a Vicat softening temperature of from about 10° C. to about 100° C., in some embodiments from about 20° C. to about 80° C., and in some embodiments, from about 30° C. to about 60° C. The semi-crystalline polyolefin may have a melting temperature of from about 20° C. to about 120° C., in some embodiments from about 35° C. to about 90° C., and in some embodiments, from about 40° C. to about 80° C. The latent heat of fusion ($\Delta H_f$) and melting temperature may be determined using differential scanning calorimetry ("DSC") in accordance with ASTM D-3417 as is well known to those skilled in the art. The Vicat softening temperature may be determined in accordance with ASTM D-1525.

Exemplary semi-crystalline polyolefins include polyethylene, polypropylene, blends and copolymers thereof. In one particular embodiment, a polyethylene is employed that is a copolymer of ethylene and an $\alpha$-olefin, such as a $C_3$-$C_{20}$ $\alpha$-olefin or $C_3$-$C_{12}$ $\alpha$-olefin. Suitable $\alpha$-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted I-decene; 1-dodecene; and styrene. Particularly desired $\alpha$-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The $\alpha$-olefin content may likewise range from about 1 mole % to about 40 mole %, in some embodiments from about 1.5 mole % to about 15 mole %, and in some embodiments, from about 2.5 mole % to about 13 mole %.

The density of the polyethylene may vary depending on the type of polymer employed, but generally ranges from 0.85 to 0.96 grams per cubic centimeter ("g/cm³"). Polyethylene "plastomers", for instance, may have a density in the range of from 0.85 to 0.91 g/cm³. Likewise, "linear low density polyethylene" ("LLDPE") may have a density in the range of from 0.91 to 0.940 g/cm³; "low density polyethylene" ("LOPE") may have a density in the range of from 0.910 to 0.940 g/cm³; and "high density polyethylene" ("HOPE") may have density in the range of from 0.940 to 0.960 g/cm³. Densities may be measured in accordance with ASTM 1505.

Particularly suitable polyethylene copolymers are those that are "linear" or "substantially linear." The term "substantially linear" means that, in addition to the short chain branches attributable to comonomer incorporation, the ethylene polymer also contains long chain branches in that the polymer backbone. "Long chain branching" refers to a chain length of at least 6 carbons. Each long chain branch may have the same comonomer distribution as the polymer backbone and be as long as the polymer backbone to which it is attached. Preferred substantially linear polymers are substituted with from 0.01 long chain branch per 1000 carbons to 1 long chain branch per 1000 carbons, and in some embodiments, from 0.05 long chain branch per 1000 carbons to 1 long chain branch per 1000 carbons. In contrast to the term "substantially linear", the term "linear" means that the polymer lacks measurable or demonstrable long chain branches. That is, the polymer is substituted with an average of less than 0.01 long chain branch per 1000 carbons.

The density of a linear ethylene/$\alpha$-olefin copolymer is a function of both the length and amount of the $\alpha$-olefin. That is, the greater length of the $\alpha$-olefin and the greater the amount of $\alpha$-olefin present, the lower the density of the copolymer. Although not necessarily required, linear polyethylene "plastomers" are particularly desirable in that the content of $\alpha$-olefin short chain branching content is such that the ethylene copolymer exhibits both plastic and elastomeric characteristics—i.e., a "plastomer." Because polymerization with $\alpha$-olefin comonomers decreases crystallinity and density, the resulting plastomer normally has a density lower than that of polyethylene thermoplastic polymers (e.g., LLDPE), but approaching and/or overlapping that of an elastomer. For example, the density of the polyethylene plastomer may be 0.91 grams per cubic centimeter (g/cm³) or less, in some embodiments, from 0.85 to 0.88 g/cm³, and in some embodiments, from 0.85 g/cm³ to 0.87 g/cm³. Despite having a density similar to elastomers, plastomers generally exhibit a higher degree of crystallinity, are relatively non-tacky, and may be formed into pellets that are non-adhesive and relatively free flowing.

The distribution of the $\alpha$-olefin comonomer within a polyethylene plastomer is typically random and uniform among the differing molecular weight fractions forming the ethylene copolymer. This uniformity of comonomer distribution within the plastomer may be expressed as a comonomer distribution breadth index value ("CDBI") of 60 or more, in some embodiments 80 or more, and in some embodiments, 90 or more. Further, the polyethylene plastomer may be characterized by a DSC melting point curve that exhibits the occurrence of a single melting point peak occurring in the region of 50 to 110° C. (second melt rundown).

Preferred plastomers for use in the present invention are ethylene-based copolymer plastomers available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai, et al.; and U.S. Pat. No. 5,278,272 to Lai, et al., which are incorporated herein in their entirety by reference thereto for all purposes.

Of course, the present invention is by no means limited to the use of ethylene polymers. For instance, propylene polymers may also be suitable for use as a semi-crystalline polyolefin. Suitable plastomeric propylene polymers may include, for instance, copolymers or terpolymers of propylene include copolymers of propylene with an α-olefin (e.g., $C_3$-$C_{20}$), such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some embodiments from about 1 wt. % to about 20 wt. %, and in some embodiments, from about 2 wt. % to about 10 wt. %. Preferably, the density of the polypropylene (e.g., propylene/α-olefin copolymer) may be 0.91 grams per cubic centimeter (g/cm$^3$) or less, in some embodiments, from 0.85 to 0.88 g/cm$^3$, and in some embodiments, from 0.85 g/cm$^3$ to 0.87 g/cm$^3$. Suitable propylene polymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al., which are incorporated herein in their entirety by reference thereto for all purposes.

Any of a variety of known techniques may generally be employed to form the semi-crystalline polyolefins. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et al., which are incorporated herein in their entirety by reference thereto for all purposes. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

The melt flow index (MI) of the semi-crystalline polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 5000 grams in 10 minutes at 190° C., and may be determined in accordance with ASTM Test Method D1238-E.

Of course, other thermoplastic polymers may also be used to form the elastic film, either alone or in conjunction with the semi-crystalline polyolefins. For instance, a substantially amorphous block copolymer may be employed that has at least two blocks of a monoalkenyl arene polymer separated by at least one block of a saturated conjugated diene polymer. The monoalkenyl arene blocks may include styrene and its analogues and homologues, such as o-methyl styrene; p-methyl styrene; p-tert-butyl styrene; 1,3 dimethyl styrene p-methyl styrene; etc., as well as other monoalkenyl polycyclic aromatic compounds, such as vinyl naphthalene; vinyl anthrycene; and so forth. Preferred monoalkenyl arenes are styrene and p-methyl styrene. The conjugated diene blocks may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene (butadiene); 2-methyl-1,3 butadiene; isoprene; 2,3 dimethyl-1,3 butadiene; 1,3 pentadiene (piperylene); 1,3 hexadiene; and so forth.

The amount of monoalkenyl arene (e.g., polystyrene) blocks may vary, but typically constitute from about 8 wt. % to about 55 wt. %, in some embodiments from about 10 wt. % to about 35 wt. %, and in some embodiments, from about 25 M. % to about 35 wt. % of the copolymer. Suitable block copolymers may contain monoalkenyl arene endblocks having a number average molecular weight from about 5,000 to about 35,000 and saturated conjugated diene midblocks having a number average molecular weight from about 20,000 to about 170,000. The total number average molecular weight of the block polymer may be from about 30,000 to about 250,000.

Particularly suitable thermoplastic elastomeric copolymers are available from Kraton Polymers LLC of Houston, Tex. under the trade name KRATON®. KRATON® polymers include styrene-diene block copolymers, such as styrene-butadiene, styrene-isoprene, styrene-butadiene-styrene, and styrene-isoprene-styrene. KRATON® polymers also include styrene-olefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. These block copolymers may have a linear, radial or star-shaped molecular configuration. Specific KRATON® block copolymers include those sold under the brand names G 1652, G 1657, G 1730, MD6673, and MD6973. Various suitable styrenic block copolymers are described in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

The amount of elastomeric polymer(s) employed in the film may vary, but is typically about 30 wt. % or more of the film, in some embodiments about 50 wt. % or more, and in some embodiments, about 80 wt. % or more of the of the film. In one embodiment, for example, the semi-crystalline polyolefin(s) constitute about 70 wt. % or more of the film, in some embodiments about 80 wt. % or more of the film, and in some embodiments, about 90 wt. % or more of the film. In other embodiments, blends of semi-crystalline polyolefin(s) and elastomeric block copolymer(s) may be employed. In such embodiments, the block copolymer(s) may constitute from about 5 wt. % to about 50 wt. %, in some embodiments from about 10 wt. % to about 40 wt. %, and in some embodiments, from about 15 wt. % to about 35 wt. % of the blend. Likewise, the semi-crystalline polyolefin(s) may constitute from about 50 wt. % to about 95 wt. %, in some embodiments from about 60 wt. % to about 90 wt. %, and in some embodiments, from about 65 wt. % to about 85 wt. % of the blend. It should of course be understood that other elastomeric and/or non-elastomeric polymers may also be employed in the film.

Besides polymers, the elastic film of the present invention may also contain other components as is known in the art. In one embodiment, for example, the elastic film contains a filler. Fillers are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. Nos. 5,997,981; 6,015,764; and 6,111,163 to McCormack, et al.; U.S. Pat. No. 5,932,497 to Morman, et al.; U.S. Pat. No. 6,461,457 to Taylor, et al., which are incorporated herein in their entirety by reference thereto for all purposes.

The fillers may have a spherical or non-spherical shape with average particle sizes in the range of from about 0.1 to about 7 microns. Examples of suitable fillers include, but are not limited to, calcium carbonate, various kinds of clay, silica, alumina, barium carbonate, sodium carbonate, magnesium carbonate, talc, barium sulfate, magnesium sulfate, aluminum sulfate, titanium dioxide, zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as stearic acid, may also be applied to the filler particles if desired. When utilized, the filler content may vary, such as from about 25 wt. % to about 75 wt. %, in some embodiments, from about 30 wt. % to about 70 wt. %, and in some embodiments, from about 40 wt. % to about 60 wt. % of the film.

Other additives may also be incorporated into the film, such as melt stabilizers, processing stabilizers, heat stabilizers, light stabilizers, antioxidants, heat aging stabilizers, whitening agents, antiblocking agents, bonding agents, tackifiers, viscosity modifiers, etc. Examples of suitable tackifier resins may include, for instance, hydrogenated hydrocarbon resins. REGALREZ™ hydrocarbon resins are examples of such hydrogenated hydrocarbon resins, and are available from Eastman Chemical. Other tackifiers are available from ExxonMobil under the ESCOREZ™ designation. Viscosity modifiers may also be employed, such as polyethylene wax (e.g., EPOLENE™ C-10 from Eastman Chemical). Phosphite stabilizers (e.g., IRGAFOS available from Ciba Specialty Chemicals of Terrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals) are exemplary heat and light stabilizers. Further, hindered phenols are commonly used as an antioxidant in the production of films. Some suitable hindered phenols include those available from Ciba Specialty Chemicals of under the trade name "Irganox®", such as Irganox® 1076, 1010, or E 201. Moreover, bonding agents may also be added to the film to facilitate bonding of the film to additional materials (e.g., nonwoven web). When employed, such additives (e.g., tackifier, antioxidant, stabilizer, etc.) may each be present in an amount from about 0.001 wt. % to about 25 wt. %, in some embodiments, from about 0.005 wt. % to about 20 wt. %, and in some embodiments, from 0.01 wt. % to about 15 wt. % of the film.

The elastic film of the present invention may be mono- or multi-layered. Multilayer films may be prepared by co-extrusion of the layers, extrusion coating, or by any conventional layering process. Such multilayer films normally contain at least one base layer and at least one skin layer, but may contain any number of layers desired. For example, the multilayer film may be formed from a base layer and one or more skin layers, wherein the base layer is formed from a semi-crystalline polyolefin. In such embodiments, the skin layer(s) may be formed from any film-forming polymer. If desired, the skin layer(s) may contain a softer, lower melting polymer or polymer blend that renders the layer(s) more suitable as heat seal bonding layers for thermally bonding the film to a nonwoven web. For example, the skin layer(s) may be formed from an olefin polymer or blends thereof, such as described above. Additional film-forming polymers that may be suitable for use with the present invention, alone or in combination with other polymers, include ethylene vinyl acetate, ethylene ethyl acrylate, ethylene acrylic acid, ethylene methyl acrylate, ethylene normal butyl acrylate, nylon, ethylene vinyl alcohol, polystyrene, polyurethane, and so forth.

The thickness of the skin layer(s) is generally selected so as not to substantially impair the elastomeric properties of the film. To this end, each skin layer may separately comprise from about 0.5% to about 15% of the total thickness of the film, and in some embodiments from about 1% to about 10% of the total thickness of the film. For instance, each skin layer may have a thickness of from about 0.1 to about 10 micrometers, in some embodiments from about 0.5 to about 5 micrometers, and in some embodiments, from about 1 to about 2.5 micrometers. Likewise, the base layer may have a thickness of from about 1 to about 40 micrometers, in some embodiments from about 2 to about 25 micrometers, and in some embodiments, from about 5 to about 20 micrometers.

The properties of the resulting film may generally vary as desired. For instance, prior to stretching, the film typically has a basis weight of about 100 grams per square meter or less, and in some embodiments, from about 50 to about 75 grams per square meter. Upon stretching, the film typically has a basis weight of about 60 grams per square meter or less, and in some embodiments, from about 15 to about 35 grams per square meter. The stretched film may also have a total thickness of from about 1 to about 100 micrometers, in some embodiments, from about 10 to about 80 micrometers, and in some embodiments, from about 20 to about 60 micrometers.

II. Nonwoven Web Material

As will be described in more detail below, the polymers used to form the nonwoven web material typically have a softening temperature that is higher than the temperature imparted during bonding. In this manner, the polymers do not substantially soften during bonding to such an extent that the fibers of the nonwoven web material become completely melt flowable. For instance, polymers may be employed that have a Vicat softening temperature (ASTM D-1525) of from about 100° C. to about 300° C., in some embodiments from about 120° C. to about 250° C., and in some embodiments, from about 130° C. to about 200° C. Exemplary high-softening point polymers for use in forming nonwoven web materials may include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. If desired, biodegradable polymers, such as those described above, may also be employed. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. It should be noted that the polymer(s) may also contain other additives, such as processing aids or treatment compositions to impart desired properties to the fibers, residual amounts of solvents, pigments or colorants, and so forth.

Monocomponent and/or multicomponent fibers may be used to form the nonwoven web material. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. and so forth. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Krueqe, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference thereto for all purposes. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Larqman, et al., and U.S. Pat. No. 5,057,368 to Larqman, et al., which are incorporated herein in their entirety by reference thereto for all purposes.

Although any combination of polymers may be used, the polymers of the multicomponent fibers are typically made from thermoplastic materials with different glass transition or melting temperatures where a first component (e.g., sheath) melts at a temperature lower than a second component (e.g., core). Softening or melting of the first polymer component of the multicomponent fiber allows the multicomponent fibers to form a tacky skeletal structure, which upon cooling, stabilizes the fibrous structure. For example, the multicomponent fibers may have from about 20% to about 80%, and in some embodiments, from about 40% to about 60% by weight of the low melting polymer. Further, the multicomponent fibers may have from about 80% to about 20%, and in some embodiments, from about 60% to about 40%, by weight of the high melting polymer. Some examples of known sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del.

Fibers of any desired length may be employed, such as staple fibers, continuous fibers, etc. In one particular embodiment, for example, staple fibers may be used that have a fiber length in the range of from about 1 to about 150 millimeters, in some embodiments from about 5 to about 50 millimeters, in some embodiments from about 10 to about 40 millimeters, and in some embodiments, from about 10 to about 25 millimeters. Although not required, carding techniques may be employed to form fibrous layers with staple fibers as is well known in the art. For example, fibers may be formed into a carded web by placing bales of the fibers into a picker that separates the fibers. Next, the fibers are sent through a combing or carding unit that further breaks apart and aligns the fibers in the machine direction so as to form a machine direction-oriented fibrous nonwoven web. The carded web may then be bonded using known techniques to form a bonded carded nonwoven web.

If desired, the nonwoven web material used to form the nonwoven composite may have a multi-layer structure. Suitable multi-layered materials may include, for instance, spunbond/meltblown/spunbond (SMS) laminates and spunbond/meltblown (SM) laminates. Various examples of suitable SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., which are incorporated herein in their entirety by reference thereto for all purposes. In addition, commercially available SMS laminates may be obtained from Kimberly-Clark Corporation under the designations Spunguard® and Evolution®.

Another example of a multi-layered structure is a spunbond web produced on a multiple spin bank machine in which a spin bank deposits fibers over a layer of fibers deposited from a previous spin bank. Such an individual spunbond nonwoven web may also be thought of as a multi-layered structure. In this situation, the various layers of deposited fibers in the nonwoven web may be the same, or they may be different in basis weight and/or in terms of the composition, type, size, level of crimp, and/or shape of the fibers produced. As another example, a single nonwoven web may be provided as two or more individually produced layers of a spunbond web, a carded web, etc., which have been bonded together to form the nonwoven web. These individually produced layers may differ in terms of production method, basis weight, composition, and fibers as discussed above.

A nonwoven web material may also contain an additional fibrous component such that it is considered a composite. For example, a nonwoven web may be entangled with another fibrous component using any of a variety of entanglement techniques known in the art (e.g., hydraulic, air, mechanical, etc.). In one embodiment, the nonwoven web is integrally entangled with cellulosic fibers using hydraulic entanglement. A typical hydraulic entangling process utilizes high pressure jet streams of water to entangle fibers to form a highly entangled consolidated fibrous structure, e.g., a nonwoven web. Hydraulically entangled nonwoven webs of staple length and continuous fibers are disclosed, for example, in U.S. Pat. No. 3,494,821 to Evans and U.S. Pat. No. 4,144,370 to Boulton, which are incorporated herein in their entirety by reference thereto for all purposes. Hydraulically entangled composite nonwoven webs of a continuous fiber nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes. The fibrous component of the composite may contain any desired amount of the resulting substrate. The fibrous component may contain greater than about 50% by weight of the composite, and in some embodiments, from about 60% to about 90% by weight of the composite. Likewise, the nonwoven web may contain less than about 50% by weight of the composite, and in some embodiments, from about 10% to about 40% by weight of the composite.

Although not required, the nonwoven web material may necked in one or more directions prior to lamination to the film of the present invention. Suitable techniques necking techniques are described in U.S. Pat. Nos. 5,336,545, 5,226,992, 4,981,747 and 4,965,122 to Morman, as well as U.S. Patent Application Publication No. 2004/0121687 to Morman, et al. Alternatively, the nonwoven web may remain relatively inextensible in at least one direction prior to lamination to the film. In such embodiments, the nonwoven web may be optionally stretched in one or more directions subsequent to lamination to the film.

The basis weight of the nonwoven web material may generally vary, such as from about 5 grams per square meter ("gsm") to 120 gsm, in some embodiments from about 10 gsm to about 70 gsm, and in some embodiments, from about 15 gsm to about 35 gsm. When multiple nonwoven web materials, such materials may have the same or different basis weights.

III. Lamination Technique

To concurrently form apertures and bonds between the film and the nonwoven web material, lamination is generally accomplished in the present invention via a patterned bonding technique (e.g., thermal point bonding, ultrasonic bonding, etc.) in which the materials are supplied to a nip defined by at least one patterned roll. Thermal point bonding, for instance, typically employs a nip formed between two rolls, at least one of which is patterned. Ultrasonic bonding, on the other hand, typically employs a nip formed between a sonic horn and a patterned roll. Regardless of the technique chosen, the patterned roll contains a plurality of raised bonding elements to concurrently bond the film to the nonwoven web material(s) and form apertures in the film. The size of the bonding elements may be specifically tailored to facilitate the formation of apertures in the film and enhance bonding between the film and the nonwoven material(s). For example, the bonding elements are typically selected to have a relatively large length dimension. The length dimension of the bonding elements may be from about 300 to about 5000 micrometers, in some embodiments from about 500 to about 4000 micrometers, and in some embodiments, from about 1000 to about 2000 micrometers. The width dimension of the bonding elements may likewise range from about 20 to about 500 micrometers, in some embodiments from about 40 to about 200 micrometers, and in some embodiments, from about 50 to about 150 micrometers. In addition, the "element aspect ratio" (the ratio of the length of an element to its width) may range from about 2 to about 100, in some embodiments from about 4 to about 50, and in some embodiments, from about 5 to about 20.

Besides the size of the bonding elements, the overall bonding pattern may also be selectively controlled to achieve the desired aperture formation. In one embodiment, for example, a bonding pattern is selected in which the longitudinal axis (longest dimension along a center line of the element) of one or more of the bonding elements is skewed relative to the machine direction ("MD") of the elastic film. For example, one or more of the bonding elements may be oriented from about 30° to about 150°, in some embodiments from about 45° to about 135°, and in some embodiments, from about 60° to about 120° relative to the machine direction of the film. In this manner, the bonding elements will present a relatively large surface to the film in a direction substantially perpendicular to that which the film moves. This increases the area over which shear stress is imparted to the film and, in turn, facilitates aperture formation.

Figure 2:
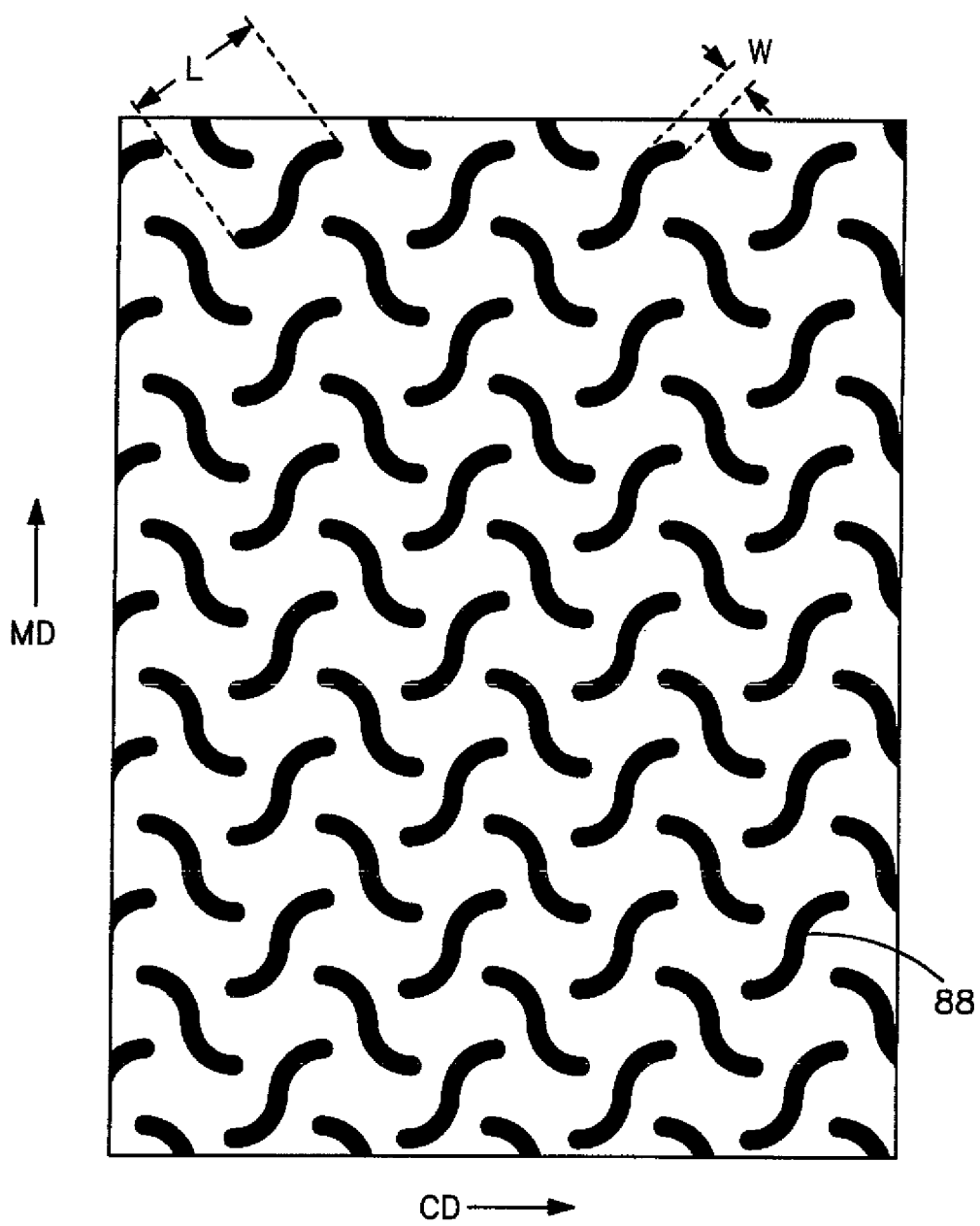
FIG. 2 illustrates one embodiment of an "S-weave" bonding pattern that may be used in accordance with the present invention.
Figure 3:
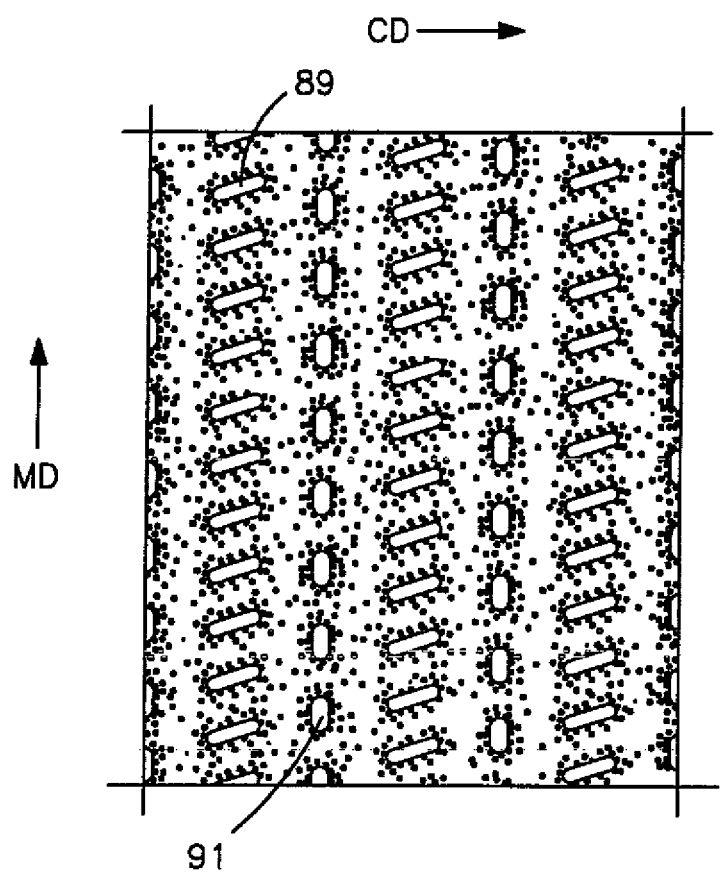
FIG. 3 illustrates one embodiment of a "rib-knit" bonding pattern that may be used in accordance with the present invention.
Figure 4:
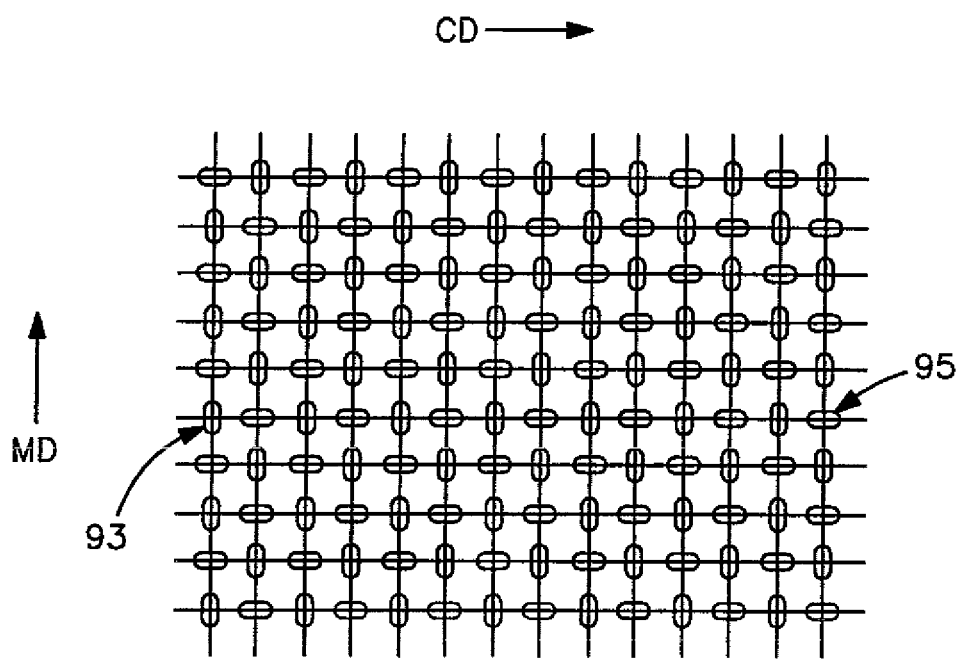
FIG. 4 illustrates one embodiment of a "wire-weave" bonding pattern that may be used in accordance with the present invention.

The pattern of the bonding elements is generally selected so that the nonwoven composite has a total bond area of less than about 50% (as determined by conventional optical microscopic methods), and in some embodiments, less than about 30%. The bond density is also typically greater than about 50 bonds per square inch, and in some embodiments, from about 75 to about 500 pin bonds per square inch. One suitable bonding pattern for use in the present invention is known as an "S-weave" pattern and is described in U.S. Pat. No. 5,964,742 to McCormack, et al., which is incorporated herein in its entirety by reference thereto for all purposes. S-weave patterns typically have a bonding element density of from about 50 to about 500 bonding elements per square inch, and in some embodiments, from about 75 to about 150 bonding elements per square inch. An example of a suitable "S-weave" pattern in shown in FIG. 2, which illustrates S-shaped bonding elements 88 having a length dimension "L" and a width dimension "W." Another suitable bonding pattern is known as the "rib-knit" pattern and is described in U.S. Pat. No. 5,620,779 to Levy, et al., which is incorporated herein in its entirety by reference thereto for all purposes. Rib-knit patterns typically have a bonding element density of from about 150 to about 400 bonding elements per square inch, and in some embodiments, from about 200 to about 300 bonding elements per square inch. An example of a suitable "rib-knit" pattern in shown in FIG. 3, which illustrates bonding elements 89 and bonding elements 91, which are oriented in a different direction. Yet another suitable pattern is the "wire weave" pattern, which has a bonding element density of from about 200 to about 500 bonding elements per square inch, and in some embodiments, from about 250 to about 350 bonding elements per square inch. An example of a suitable "wire-weave" pattern in shown in FIG. 4, which illustrates bonding elements 93 and bonding elements 95, which are oriented in a different direction. Other bond patterns that may be used in the present invention are described in U.S. Pat. No. 3,855,046 to Hansen et al.; U.S. Pat. No. 5,962,112 to Haynes et al.; U.S. Pat. No. 6,093,665 to Sayovitz et al.; U.S. Pat. No. D375,844 to Edwards, et al.; U.S. Pat. No. D428,267 to Romano et al.; and U.S. Pat. No. D390,708 to Brown, which are incorporated herein in their entirety by reference thereto for all purposes.

The selection of an appropriate bonding temperature (e.g., the temperature of a heated roll) will help melt and/soften the low-softening point elastomeric polymer(s) of the film at regions adjacent to the bonding elements. The softened elastomeric polymer(s) may then flow and become displaced during bonding, such as by pressure exerted by the bonding elements. The displaced portions of the film surrounding the apertures can also fuse to the nonwoven web material(s), thereby forming an integral nonwoven composite. Furthermore, because the elastomeric polymer(s) may physically entrap or adhere to the fibers at the bond sites, adequate bond formation may be achieved without requiring substantial softening of the polymer(s) used to form the nonwoven web material. Thus, the nonwoven web material remains substantially unbonded to the film or other materials at those regions located directly adjacent to (e.g. above or below) the apertures. Further, the nonwoven web material is also generally unapertured, although it may of course develop some small cuts or tears during processing.

To achieve such concurrent aperture and bond formation without substantially softening the polymer(s) of the nonwoven web material, the bonding temperature and pressure may be selectively controlled. For example, one or more rolls may be heated to a surface temperature of from about 50° C. to about 160° C., in some embodiments from about 60° C. to about 140° C., and in some embodiments, from about 70° C. to about 120° C. Likewise, the pressure exerted by rolls ("nip pressure") during thermal bonding may range from about 75 to about 600 pounds per linear inch, in some embodiments from about 100 to about 400 pounds per linear inch, and in some embodiments, from about 120 to about 200 pounds per linear inch. Of course, the residence time of the materials may influence the particular bonding parameters employed.

As stated, another factor that influences concurrent aperture and bond formation is the degree of tension in the film during lamination. An increase in film tension, for example, typically correlates to an increase in aperture size. Of course, a film tension that is too high may adversely affect the integrity of the film. Thus, in most embodiments of the present invention, a stretch ratio of about 1.5 or more, in some embodiments from about 2.5 to about 7.0, and in some embodiments, from about 3.0 to about 5.5, is employed to achieve the desired degree of tension in the film during lamination. The stretch ratio may be determined by dividing the final length of the film by its original length. The stretch ratio may also be approximately the same as the draw ratio, which may be determined by dividing the linear speed of the film during lamination (e.g., speed of the nip rolls) by the linear speed at which the film is formed (e.g., speed of casting rolls or blown nip rolls).

The film may be "pre-stretched" (prior to lamination) by rolls rotating at different speeds of rotation so that the sheet is stretched to the desired stretch ratio in the machine direction. This uniaxially stretched film may also be oriented in the cross-machine direction to form a "biaxially stretched" film. The orientation temperature profile during the "pre-stretching" operation is generally below the melting point of one or more polymers in the film, but high enough to enable the composition to be drawn or stretched. For example, the film may be stretched at a temperature from about 15° C. to about 50° C., in some embodiments from about 25° C. to about 40° C., and in some embodiments, from about 30° C. to about 40° C. When "pre-stretched" in the manner described above, the degree of stretch during lamination may be increased, maintained, or slightly reduced (retracted) to desired degree of tension.

Upon lamination, the elastic film is bonded to the nonwoven web material(s) and apertured. The size and/or pattern of the resulting apertures generally correspond to the size and/or pattern of the bonding elements. That is, the apertures may have a length, width, aspect ratio, and orientation as described above. For example, the length dimension of the apertures may be from about 200 to about 5000 micrometers, in some embodiments from about 350 to about 4000 micrometers, and in some embodiments, from about 500 to about 2500 micrometers. The width dimension of the apertures may likewise range from about 20 to about 500 micrometers, in some embodiments from about 40 to about 200 micrometers, and in some embodiments, from about 50 to about 150 micrometers. In addition, the "aspect ratio" (the ratio of the length of an aperture to its width) may range from about 2 to about 100, in some embodiments from about 4 to about 50, and in some embodiments, from about 5 to about 20. Similarly, the longitudinal axis of one or more of the apertures (longest dimension along a center line of the aperture) may be skewed relative to the machine direction of the elastic film, such as from about 30° to about 150°, in some embodiments from about 45° to about 135°, and in some embodiments, from about 60° to about 120° relative to the machine direction of the film.

Various embodiments of the present invention will now be described in greater detail. Of course, it should be understood that the description provided below is merely exemplary, and that other methods are contemplated by the present invention. Referring to FIG. 1, for instance, one embodiment of a method for forming a composite from an elastic film and a nonwoven web material is shown. As shown, the raw materials of the film (e.g., elastomeric polymer) may be dry mixed together (i.e., without a solvent) and added to a hopper (not shown) of an extrusion apparatus 40. The raw materials may alternatively be blended with a solvent. In the hopper, the materials are dispersively mixed in the melt and compounded using any known technique, such as batch and/or continuous compounding techniques that employ, for example, a Banbury mixer, Farrel continuous mixer, single screw extruder, twin screw extruder, etc.

Any known technique may be used to form a film from the compounded material, including blowing, casting, flat die extruding, etc. In one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al., all of which are incorporated herein in their entirety by reference thereto for all purposes. For example, in the particular embodiment of FIG. 1, the compounded material (not shown) is supplied to the extrusion apparatus 40 and then blown into nip rolls 42 to form a single-layered precursor elastic film 10. The rolls 42 may be kept at temperature sufficient to solidify and quench the precursor elastic film 10 as it is formed, such as from about 20 to 60° C. Typically, the resulting precursor elastic film is generally unapertured, although it may of course possess small cuts or tears as a result of processing. The use of an initially unapertured film can provide a variety of benefits, including the avoidance of registration steps needed to align the apertures with bond sites during lamination.

Referring again to FIG. 1, one method for forming a uniaxially stretched film is shown. In the illustrated embodiment, the film 10 is stretched and thinned in the machine direction by passing it through a film-orientation unit or machine direction orienter ("MDO") 44, such as commercially available from Marshall and Willams, Co. of Providence, R.I. In the illustrated embodiment, the MDO has a plurality of stretching rolls 46 that progressively stretch and thin the film 10 in the machine direction. While four pairs of rolls 46 are illustrated in FIG. 1, it should be understood that the number of rolls may be higher or lower, depending on the level of stretch that is desired and the degrees of stretching between each roll. The film 10 may be stretched in either single or multiple discrete stretching operations. The film 10 may also be stretched in other directions. For example, the film may be clamped at its lateral edges by chain clips and conveyed into a tenter oven. In the tenter oven, the film may be drawn in the cross-machine direction to the desired stretch ratio by chain clips diverged in their forward travel.

A nonwoven web material is also employed for laminating to the elastic film 10. For example, the nonwoven web material may simply be unwound from a supply roll. Alternatively, as shown in FIG. 1, a nonwoven web material 30 may be formed in-line, such as by spunbond extruders 48. The extruders 48 deposit fibers 50 onto a forming wire 52, which is part of a continuous belt arrangement that circulates around a series of rolls. If desired, a vacuum (not shown) may be utilized to maintain the fibers on the forming wire 52. The spunbond fibers 50 form a mat 54 that may optionally be compressed via compaction rolls 56. Although not necessarily required, a second material 30a originating from a supply roll 62 may also be laminated to the elastic film 10. The second material 30a may be a second nonwoven web material, film, etc.

Figure 7:
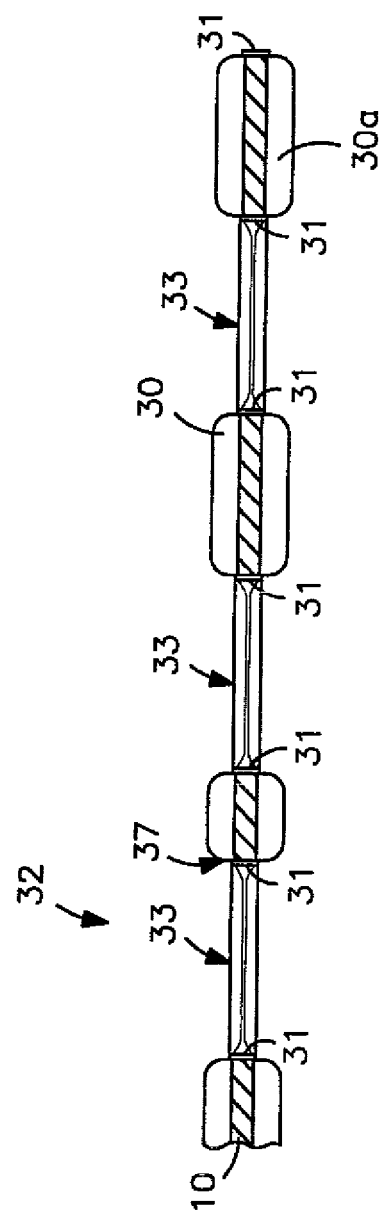
FIG. 7 is cross-sectional view of one embodiment of the nonwoven composite of the present invention.

Regardless, thermal bonding techniques are employed to laminate the material(s) to the elastic film. In FIG. 1, for instance, the materials 30 and 30a are directed to a nip defined between rolls 58 for laminating to the elastic film 10. One or both of the rolls 58 may contain a plurality of raised bonding elements and/or may be heated. Upon lamination, the elastic film 10 is melt fused to the nonwoven web materials 30 and 30a at a plurality of discrete bond sites 31. (See FIG. 7). That is, the elastomeric polymer(s) of the film 10 are softened and/or melted so that they may physically entrap fibers of the nonwoven web materials 30 and 30a. Of course, the elastic film 10 may possess a certain tack so that it also adheres to the fibers upon lamination. As shown in FIG. 7, the bond sites 31 may be located proximate (adjacent or near to) a perimeter 37 defined by corresponding apertures 33, which are formed by displacement of the film 10. The particular location of the bond sites 31 adjacent to or near the apertures 33 may enhance the integrity of the resulting composite 32 by strengthening the area surrounding the apertures 33. Because thermal bonding occurs at a temperature that is insufficient to substantially soften the polymer(s) of the nonwoven web materials 30 and 30a, as described above, they are not substantially melt fused to each other. In this manner, the composite 32 may better retain the physical properties (e.g., liquid permeability, softness, bulk, and hand feel) of the individual nonwoven web materials.

The resulting composite 32 may then be wound and stored on a take-up roll 60. Optionally, the composite 32 is kept under tension, such as by using the same linear velocity for the roll 60 as the speed of one or more of the stretching rolls 46. More preferably, however, the composite 32 is allowed to slightly retract prior to winding on to the take-up roll 60. This may be achieved by using a slower linear velocity for the roll 60. Because the elastic film 10 is tensioned prior to lamination, it will retract toward its original machine direction length and become shorter in the machine direction, thereby buckling or forming gathers in the composite. The resulting elastic composite thus becomes extensible in the machine direction to the extent that the gathers or buckles in the web may be pulled back out flat and allow the elastic film 10 to elongate.

While not shown in FIG. 1, various additional potential processing and/or finishing steps known in the art, such as slitting, treating, printing graphics, etc., may be performed without departing from the spirit and scope of the invention. For instance, the composite may optionally be mechanically stretched in the cross-machine and/or machine directions to enhance extensibility. In one embodiment, the composite may be coursed through two or more rolls that have grooves in the CD and/or MD directions. Such grooved satellite/anvil roll arrangements are described in U.S. Patent Application Publication Nos. 2004/0110442 to Rhim, et al. and 2006/0151914 to Gerndt, et al., which are incorporated herein in their entirety by reference thereto for all purposes. For instance, the laminate may be coursed through two or more rolls that have grooves in the CD and/or MD directions. The grooved rolls may be constructed of steel or other hard material (such as a hard rubber).

Figure 5:
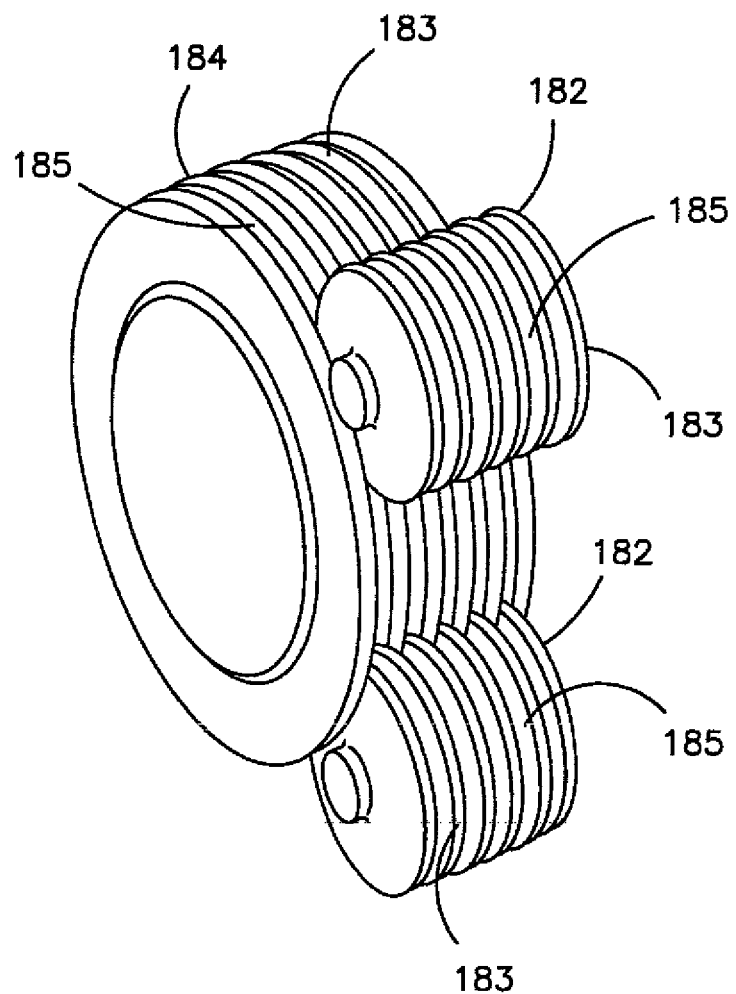
FIG. 5 is a perspective view of grooved rolls that may be used in one embodiment of the present invention.
Figure 6:
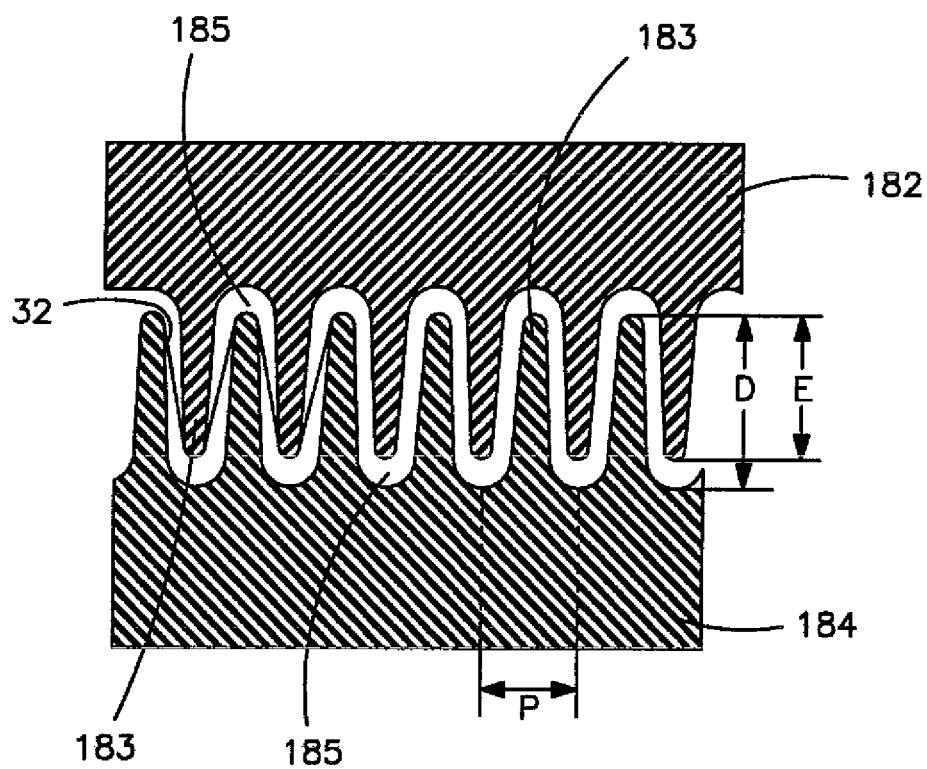
FIG. 6 is a cross-sectional view showing the engagement between two of the grooved rolls of FIG. 5.

FIGS. 5-6 further illustrate the manner in which groove rolls may incrementally stretch the composite. As shown, for example, satellite rolls 182 may engage an anvil roll 184, each of which include a plurality of ridges 183 defining a plurality of grooves 185 positioned across the grooved rolls in the cross-machine direction. The grooves 185 are generally oriented perpendicular to the direction of stretch of the material. In other words, the grooves 185 are oriented in the machine direction to stretch the composite in the cross-machine direction. The grooves 185 may likewise be oriented in the cross-machine direction to stretch the composite in the machine direction. The ridges 183 of satellite roll 182 intermesh with the grooves 185 of anvil roll 184, and the grooves 185 of satellite roll 182 intermesh with the ridges 183 of anvil roll 184.

The dimensions and parameters of the grooves 185 and ridges 183 may have a substantial effect on the degree of extensibility provided by the rolls 182 and 184. For example, the number of grooves 185 contained on a roll may generally range from about 3 and 15 grooves per inch, in some embodiments from about 5 and 12 grooves per inch, and in some embodiments, from about 5 and 10 grooves per inch. The grooves 185 may also have a certain depth "D", which generally ranges from about 0.25 to about 1.0 centimeter, and in some embodiments, from about 0.4 to about 0.6 centimeters. In addition, the peak-to-peak distance "P" between the grooves 185 is typically from about 0.1 to about 0.9 centimeters, and in some embodiments, from about 0.2 to about 0.5 centimeters. Also, the groove roll engagement distance "E" between the grooves 185 and ridges 183 may be up to about 0.8 centimeters, and in some embodiments, from about 0.15 to about 0.4 centimeters. Regardless, the composite 32 (FIG. 6) may be stretched in one or more directions at a stretch ratio of from about 1.5 to about 8.0, in some embodiments by at least about 2.0 to about 6.0, and in some embodiments, from about 2.5 to about 4.5. If desired, heat may be applied to the composite just prior to or during the application of incremental stretch to cause it to relax somewhat and ease extension. Heat may be applied by any suitable method known in the art, such as heated air, infrared heaters, heated nipped rolls, or partial wrapping of the laminate around one or more heated rolls or steam canisters, etc. Heat may also be applied to the grooved rolls themselves. It should also be understood that other grooved roll arrangement are equally suitable, such as two grooved rolls positioned immediately adjacent to one another.

Besides the above-described grooved rolls, other techniques may also be used to mechanically stretch the composite in one or more directions. For example, the composite may be passed through a tenter frame that stretches the composite. Such tenter frames are well known in the art and described, for instance, in U.S. Patent Application Publication No. 2004/0121687 to Morman, et al. The composite may also be necked. Suitable techniques necking techniques are described in U.S. Pat. Nos. 5,336,545, 5,226,992, 4,981,747 and 4,965,122 to Morman, as well as U.S. Patent Application Publication No. 2004/0121687 to Morman, et al., all of which are incorporated herein in their entirety by reference thereto for all purposes.

The nonwoven composite of the present invention may be used in a wide variety of applications. As noted above, for example, the nonwoven composite may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Absorbent articles may include a substantially liquid-impermeable layer (e.g., outer cover), a liquid-permeable layer (e.g., bodyside liner, surge layer, etc.), and an absorbent core.

In one particular embodiment, the nonwoven composite of the present invention may be used to form a liquid-permeable layer (e.g., bodyside liner, surge layer) of the absorbent article. As described above, the elastic film is bonded to the nonwoven web material at discrete bond sites located proximate to the perimeter of the apertures. By selectively controlling the conditions of the lamination process, however, the nonwoven web material remains substantially unbonded (e.g., not substantially melt fused together) at the regions located adjacent to the apertures. For example, when the elastic film is positioned between two nonwoven web materials, melt bond sites are not generally formed between the nonwoven web materials at those regions adjacent to the apertures. The conditions of the lamination process may also allow the nonwoven web material(s) to remain generally unapertured at those regions adjacent to the apertures in the elastic film. The existence of such generally unbonded and unapertured regions in the nonwoven web material(s) enhances the ability of the composite to be employed as a liquid-permeable layer in an absorbent article. Namely, because the nonwoven web material is not fused together at those regions adjacent to the film apertures, a liquid may more readily flow through the nonwoven web material and into the aperture. Likewise, the absence of substantial aperturing in the nonwoven web material allows it to retain other desirable properties (e.g., bulk, softness, handfeel, etc.).

Besides liquid-permeable materials (e.g., liners, surge layers, etc.), the nonwoven composite of the present invention may have a wide variety of other uses, such as in providing an elastic waist, leg cuff/gasketing, stretchable ear, side panel, outer cover, or any other component in which elastic properties are desirable.

Figure 8:
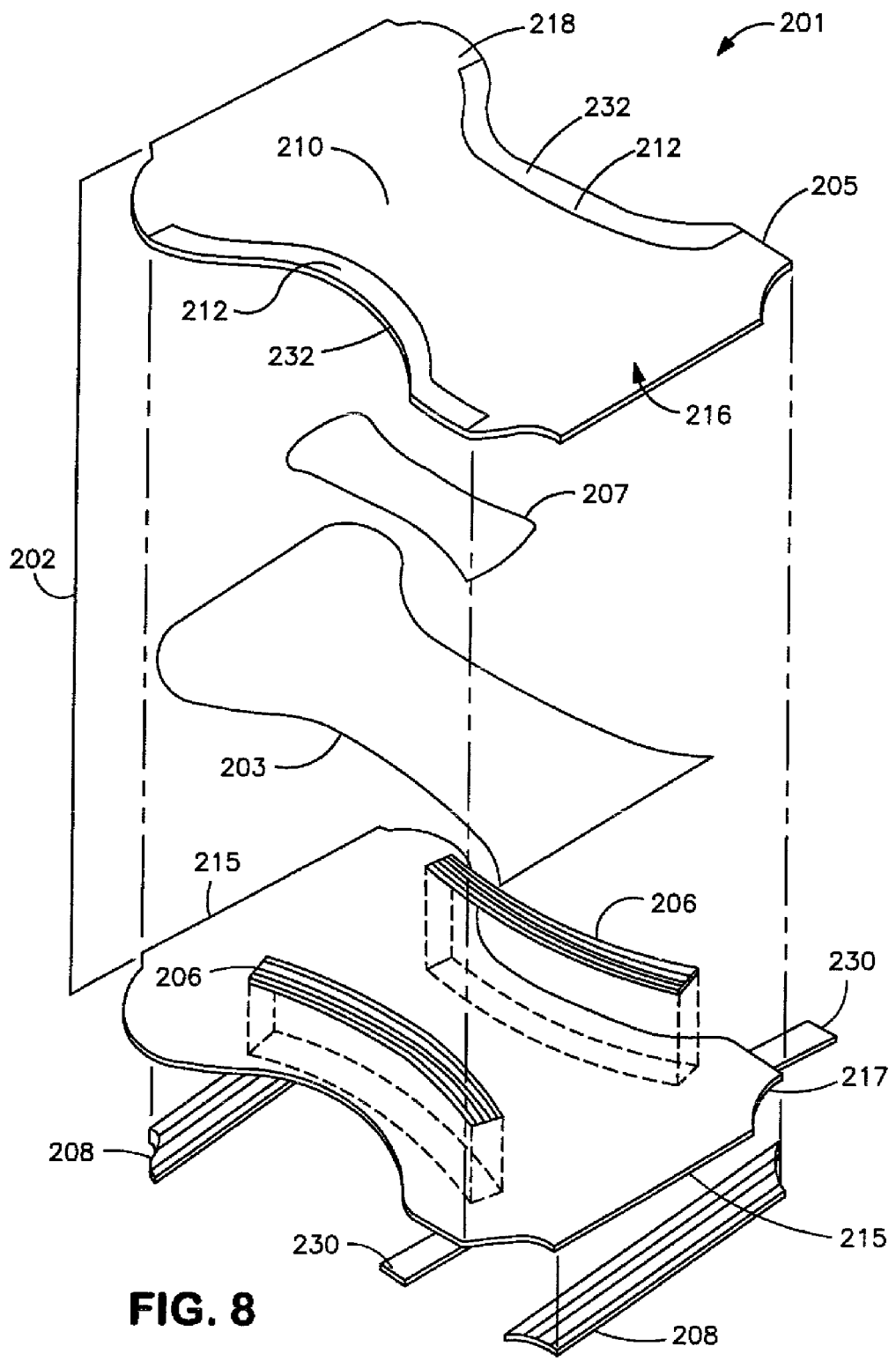
FIG. 8 is a perspective view of a personal care product that may be formed in accordance with one embodiment of the present invention.

Various embodiments of an absorbent article that may be formed according to the present invention will now be described in more detail. For purposes of illustration only, an absorbent article is shown in FIG. 8 as a diaper 201. However, as noted above, the invention may be embodied in other types of absorbent articles, such as incontinence articles, sanitary napkins, diaper pants, feminine napkins, children's training pants, and so forth. In the illustrated embodiment, the diaper 201 is shown as having an hourglass shape in an unfastened configuration. However, other shapes may of course be utilized, such as a generally rectangular shape, T-shape, or I-shape. As shown, the diaper 201 includes a chassis 202 formed by various components, including an outer cover 217, bodyside liner 205, absorbent core 203, and surge layer 207.

It should be understood, however, that other layers may also be used in the present invention. Likewise, one or more of the layers referred to in FIG. 8 may also be eliminated in certain embodiments of the present invention.

The bodyside liner 205 is generally employed to help isolate the wearer's skin from liquids held in the absorbent core 203. For example, the liner 205 presents a bodyfacing surface that is typically compliant, soft feeling, and non-irritating to the wearer's skin. Typically, the liner 205 is also less hydrophilic than the absorbent core 203 so that its surface remains relatively dry to the wearer. As indicated above, the liner 205 may be liquid-permeable to permit liquid to readily penetrate through its thickness. Exemplary liner constructions that contain a nonwoven web are described in U.S. Pat. No. 5,192,606 to Proxmire, et al.; U.S. Pat. No. 5,702,377 to Collier, IV, et al.; U.S. Pat. No. 5,931,823 to Stokes, et al.; U.S. Pat. No. 6,060,638 to Paul, et al.; and U.S. Pat. No. 6,150,002 to Varona, as well as U.S. Patent Application Publication Nos. 2004/0102750 to Jameson; 2005/0054255 to Morman, et al.; and 2005/0059941 to Baldwin, et al., all of which are incorporated herein in their entirety by reference thereto for all purposes. In one particular embodiment, the liner includes the nonwoven composite of the present invention.

As illustrated in FIG. 8, the diaper 201 may also include a surge layer 207 that helps to decelerate and diffuse surges or gushes of liquid that may be rapidly introduced into the absorbent core 203. Desirably, the surge layer 207 rapidly accepts and temporarily holds the liquid prior to releasing it into the storage or retention portions of the absorbent core 203. In the illustrated embodiment, for example, the surge layer 207 is interposed between an inwardly facing surface 216 of the bodyside liner 205 and the absorbent core 203. Alternatively, the surge layer 207 may be located on an outwardly facing surface 218 of the bodyside liner 205. The surge layer 207 is typically constructed from highly liquid-permeable materials. Examples of suitable surge layers are described in U.S. Pat. No. 5,486,166 to Ellis, et al. and U.S. Pat. No. 5,490,846 to Ellis, et al., which are incorporated herein in their entirety by reference thereto for all purposes. In one particular embodiment, the surge layer 207 includes the nonwoven composite of the present invention.

The outer cover 217 is typically formed from a material that is substantially impermeable to liquids. For example, the outer cover 217 may be formed from a thin plastic film or other flexible liquid-impermeable material. In one embodiment, the outer cover 217 is formed from a polyethylene film having a thickness of from about 0.01 millimeter to about 0.05 millimeter. The film may be impermeable to liquids, but permeable to gases and water vapor (i.e., "breathable"). This permits vapors to escape from the absorbent core 203, but still prevents liquid exudates from passing through the outer cover 217. If a more cloth-like feeling is desired, the outer cover 217 may be formed from a polyolefin film laminated to a nonwoven web. For example, a stretch-thinned polypropylene film may be thermally laminated to a spunbond web of polypropylene fibers.

Besides the above-mentioned components, the diaper 201 may also contain various other components as is known in the art. For example, the diaper 201 may also contain a substantially hydrophilic tissue wrapsheet (not illustrated) that helps maintain the integrity of the fibrous structure of the absorbent core 203. The tissue wrapsheet is typically placed about the absorbent core 203 over at least the two major facing surfaces thereof, and composed of an absorbent cellulosic material, such as creped wadding or a high wet-strength tissue. The tissue wrapsheet may be configured to provide a wicking layer that helps to rapidly distribute liquid over the mass of absorbent fibers of the absorbent core 203. The wrapsheet material on one side of the absorbent fibrous mass may be bonded to the wrapsheet located on the opposite side of the fibrous mass to effectively entrap the absorbent core 203. Furthermore, the diaper 201 may also include a ventilation layer (not shown) that is positioned between the absorbent core 203 and the outer cover 217. When utilized, the ventilation layer may help insulate the outer cover 217 from the absorbent core 203, thereby reducing dampness in the outer cover 217. Examples of such ventilation layers may include a nonwoven web laminated to a breathable film, such as described in U.S. Pat. No. 6,663,611 to Blaney, et al., which is incorporated herein in its entirety by reference thereto for all purposes.

In some embodiments, the diaper 201 may also include a pair of side panels (or ears) (not shown) that extend from the side edges 232 of the diaper 201 into one of the waist regions. The side panels may be integrally formed with a selected diaper component. For example, the side panels may be integrally formed with the outer cover 217 or from the material employed to provide the top surface. In alternative configurations, the side panels may be provided by members connected and assembled to the outer cover 217, the top surface, between the outer cover 217 and top surface, or in various other configurations. If desired, the side panels may be elasticized or otherwise rendered elastomeric by use of the elastic nonwoven composite of the present invention. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

As representatively illustrated in FIG. 8, the diaper 201 may also include a pair of containment flaps 212 that are configured to provide a barrier and to contain the lateral flow of body exudates. The containment flaps 212 may be located along the laterally opposed side edges 232 of the bodyside liner 205 adjacent the side edges of the absorbent core 203. The containment flaps 212 may extend longitudinally along the entire length of the absorbent core 203, or may only extend partially along the length of the absorbent core 203. When the containment flaps 212 are shorter in length than the absorbent core 203, they may be selectively positioned anywhere along the side edges 232 of diaper 201 in a crotch region 210. In one embodiment, the containment flaps 212 extend along the entire length of the absorbent core 203 to better contain the body exudates. Such containment flaps 212 are generally well known to those skilled in the art. For example, suitable constructions and arrangements for the containment flaps 212 are described in U.S. Pat. No. 4,704,116 to Enloe, which is incorporated herein in its entirety by reference thereto for all purposes.

To provide improved fit and to help reduce leakage of body exudates, the diaper 201 may be elasticized with suitable elastic members, as further explained below. For example, as representatively illustrated in FIG. 8, the diaper 201 may include leg elastics 206 constructed to operably tension the side margins of the diaper 201 to provide elasticized leg bands which can closely fit around the legs of the wearer to reduce leakage and provide improved comfort and appearance. Waist elastics 208 may also be employed to elasticize the end margins of the diaper 201 to provide elasticized waistbands. The waist elastics 208 are configured to provide a resilient, comfortably close fit around the waist of the wearer. The elastic nonwoven composite of the present invention is suitable for use as the leg elastics 206 and waist elastics 208. Exemplary of such materials are laminate sheets that either comprise or are adhered to the outer cover 217 so that that elastic constrictive forces are imparted thereto.

The diaper 201 may also include one or more fasteners 230. For example, two flexible fasteners 230 are illustrated in FIG. 8 on opposite side edges of waist regions to create a waist opening and a pair of leg openings about the wearer. The shape of the fasteners 230 may generally vary, but may include, for instance, generally rectangular shapes, square shapes, circular shapes, triangular shapes, oval shapes, linear shapes, and so forth. The fasteners may include, for instance, a hook-and-loop material, buttons, pins, snaps, adhesive tape fasteners, cohesives, fabric-and-loop fasteners, etc. In one particular embodiment, each fastener 230 includes a separate piece of hook material affixed to the inside surface of a flexible backing.

The various regions and/or components of the diaper 201 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the outer cover 217 and bodyside liner 205 are assembled to each other and to the absorbent core 203 using an adhesive. Alternatively, the absorbent core 203 may be connected to the outer cover 217 using conventional fasteners, such as buttons, hook and loop type fasteners, adhesive tape fasteners, and so forth. Similarly, other diaper components, such as the leg elastic members 206, waist elastic members 208 and fasteners 230, may also be assembled into the diaper 201 using any attachment mechanism.

Although various configurations of a diaper have been described above, it should be understood that other diaper and absorbent article configurations are also included within the scope of the present invention. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Several examples of such absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al., all of which are incorporated herein in their entirety by reference thereto for all purposes.

The present invention may be better understood with reference to the following examples.

Test Methods

Cycle Testing

The materials were tested using a cyclical testing procedure to determine load loss and percent set. In particular, 1-cycle testing was utilized to 150% defined elongation. For this test, the sample size was 3 inches in the cross-machine direction by 6 inches in the machine direction. The Grip size was 3 inches in width. The grip separation was 4 inches. The samples were loaded such that the machine direction of the sample was in the vertical direction. A preload of approximately 10 to 15 grams was set. The test pulled the sample to 100% elongation at a speed of 20 inches per minute, and then immediately (without pause) returned to the zero at a speed of 20 inches per minute. The results of the test data are all from the first cycle. The testing was done on a Sintech Corp. constant rate of extension tester 2/S with a Renew MTS mongoose box (control) using TESTWORKS 4.07b software (Sintech Corp, of Cary, N.C.). The tests were conducted under ambient conditions.

Air Permeability:

Air permeability was determined using the "Frazier permeability", which is measured as standard cubic feet per minute of air flow across a material, per square foot of material with an air pressure differential of 0.5 inches of water (125 Pa) across the sample. The test was performed at ambient conditions.

Peel Strength:

Values for peel strength were obtained using a specified width of fabric, clamp jaw width and a constant rate of extension. This test used two clamps, each having two jaws with each jaw having a facing in contact with the sample, to hold the material in the same plane, usually vertically, separated by 2 inches to start. The sample size was either 4 inches in width (Example 1) or 3 inches (Example 1), and had as much length as necessary to delaminate enough sample length. The jaw facing size was 1 inch high by at least 4 inches wide, and the constant rate of extension is 300 mm/min. The sample was delaminated by hand a sufficient amount to allow it to be clamped into position and the clamps move apart at the specified rate of extension to pull the laminate apart. The sample specimen was pulled apart at 180° of separation between the two layers and the peel strength reported as an average of peak load in grams. Measurement of the force was begun when 16 mm of the laminate has been pulled apart and continued until a total of 170 mm has been delaminated. The system may employ a MTS SYNERGY 200 Tensile Tester and TESTWORKS 4.08B software, which are available from MTS Systems Corporation of Eden Prairie, Minn. Results were reported as an average of three specimens and may be performed with the specimen in the cross direction (CD) or the machine direction (MD). Testing was performed at ambient conditions.

Strain:

The materials were tested to determine elongation or strain. For this test, the sample size was 3 inches in the cross-machine direction by 7 inches in the machine direction. The grip size was 3 inches in width, and intermeshing grips were utilized so that material would not slip while tested. The grip separation was 4 inches. The samples were loaded such that the machine direction of the sample was in the vertical direction. A preload of approximately 10 to 15 grams was set. The test pulled the sample until 2000 grams of tension was produced, and then the test stopped. The test speed was 500 millimeters per minute of extension or strain. The test reported the elongation or strain in percent from start when 2000 grams of tension was produced in the material. The testing was done on a Sintech Corp. constant rate of extension tester 2/S with a Renew MTS mongoose box (controller) using TESTWORKS 4.07b software (Sintech Corp, of Cary, N.C.). The tests were conducted under ambient conditions.

EXAMPLE 1

The ability to form an elastic nonwoven composite was demonstrated. The elastic film was formed from 93 wt. % of EXACT™ 5361 (ExxonMobil Chemical Co.), 5 wt. % of Dow Polyethylene 640I (Dow Chemical Co.), and 2 wt. % of SCC116921 pigment (Standridge Color Corp.). EXACT™ 5361 is a metallocene-catalyzed polyethylene plastomer having a density of 0.86 grams per cubic centimeter, a peak melting temperature of 36° C., and a melt index of 3.0 grams per 10 minutes (190° C., 2.16 kg). Dow Polyethylene 640I is a low density polyethylene having a density of 0.9215 grams per cubic centimeter, a melting point of 111° C., and a melt index of 2.0 grams per 10 minutes (190° C., 2.16 kg). The SCC116921 pigment contained titanium dioxide blended with polypropylene and polypropylene random copolymers.

The polymers were compounded by weighing appropriate portions of pellets of each polymer, combining them into one container, and mixing them together by stirring. After compounding, the film samples were blown between a collapsing nip (operated at 38 feet per minute) so that a melt temperature of about 375° F. was achieved. The blown film was thermally bonded between two polypropylene spunbond facings having a basis weight of approximately about 14 grams per square meter. Specifically, the film and facings were fed between an anvil and patterned roll (rib-knit). The patterned roll was heated to a roll surface temperature of 184° F., the anvil roll was heated to a roll surface temperature of 193° F., and the pressure was 157 pounds per linear inch. The rolls operated at a speed of 182 feet per minute so that the film was stretched in the machine direction at a stretch ratio of 4.8 (i.e., 4.8 times its original length). Once formed, the composite was then introduced into a nip of intermeshing grooved steel rolls, such as shown in FIGS. 5-6, to stretch the composite in the cross machine direction. The grooved steel rolls were heated to a temperature of 125° F. Finally, the composite was transferred to a winder, which operated at a speed of 81 feet per minute to allow in the composite to retract. The final basis weight was approximately 105 grams per square meter.

Figure 9:
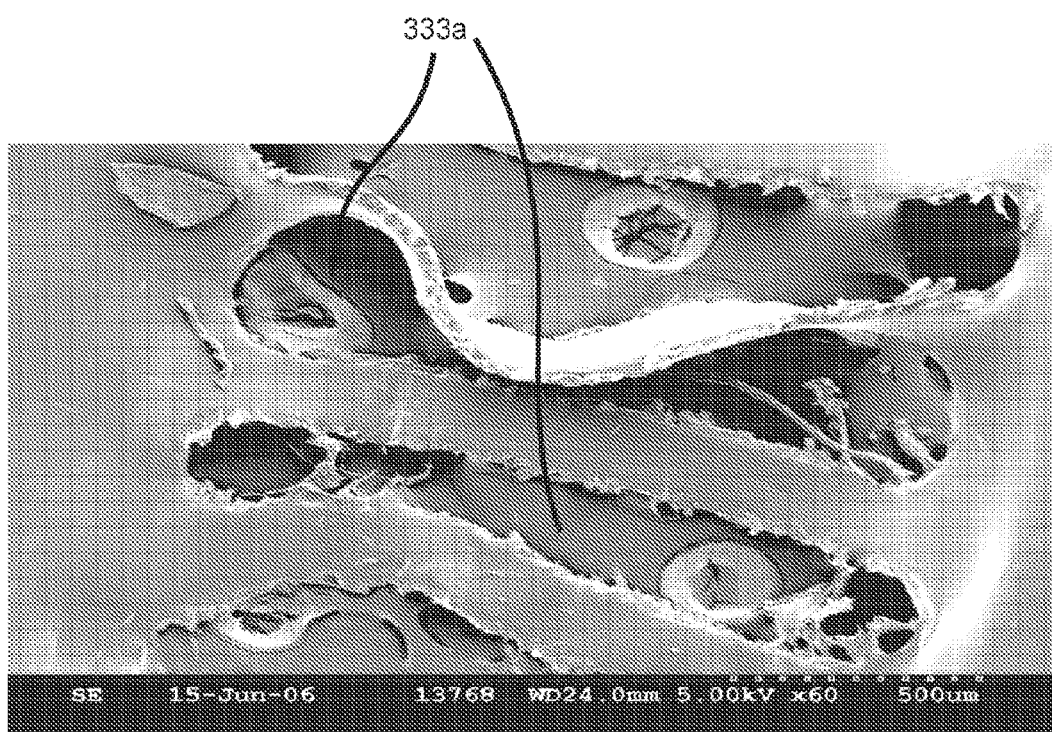
FIG. 9 is an SEM microphotograph (5 kv, 60×) of the sample formed in Example 1, showing apertures in the elastic film formed by the bars of a rib-knit bonding pattern.
Figure 10:
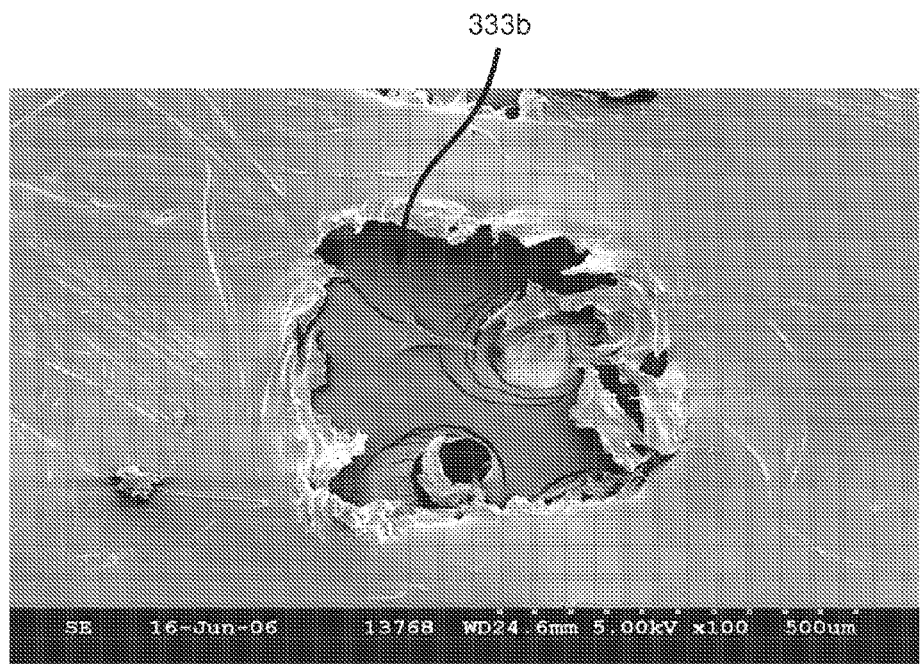
FIG. 10 is an SEM microphotograph (5 kv, 100×) of the sample formed in Example 1, showing apertures in the elastic film formed by the pins of a rib-knit bonding pattern.
Figure 11:
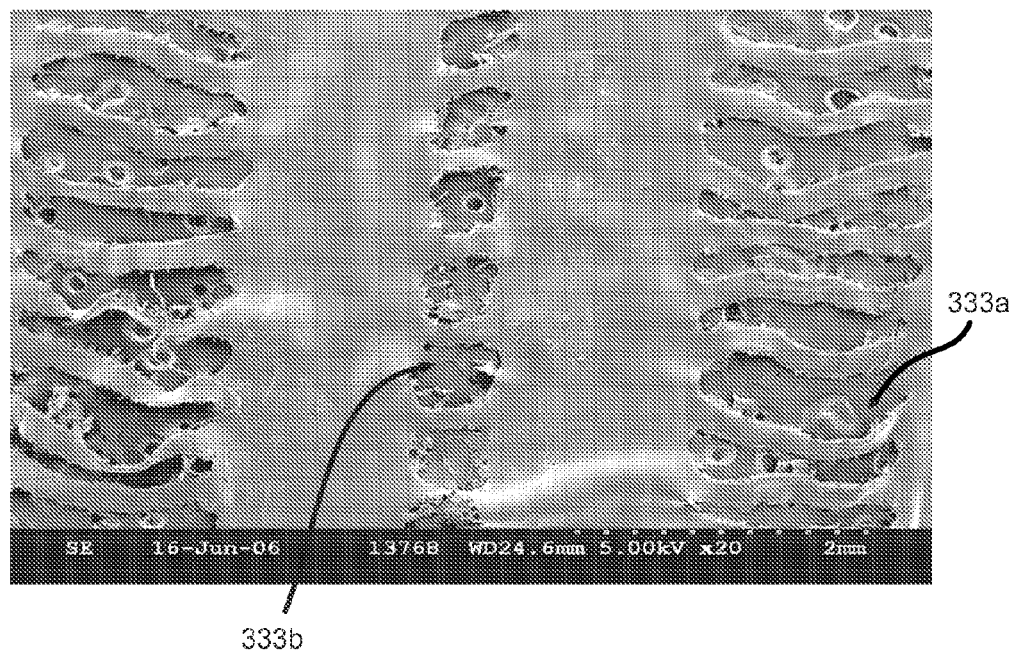
FIG. 11 is an SEM microphotograph (5 kv, 20×) of the sample formed in Example 1, showing apertures in the elastic film formed by a rib-knit bonding pattern.
Figure 12:
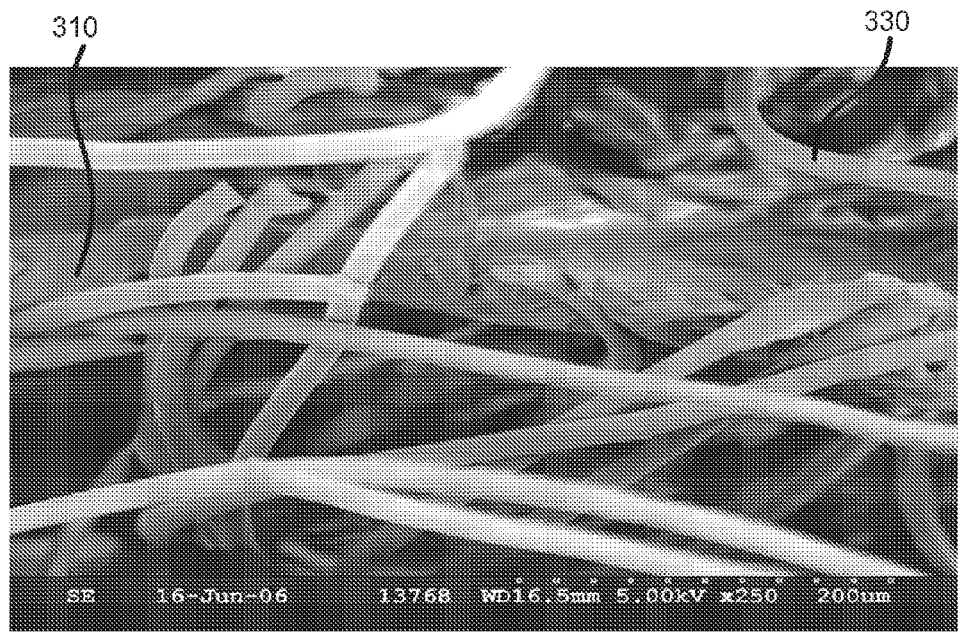
FIG. 12 is an SEM microphotograph (5 kv, 250×) of the sample formed in Example 1.
Figure 13:
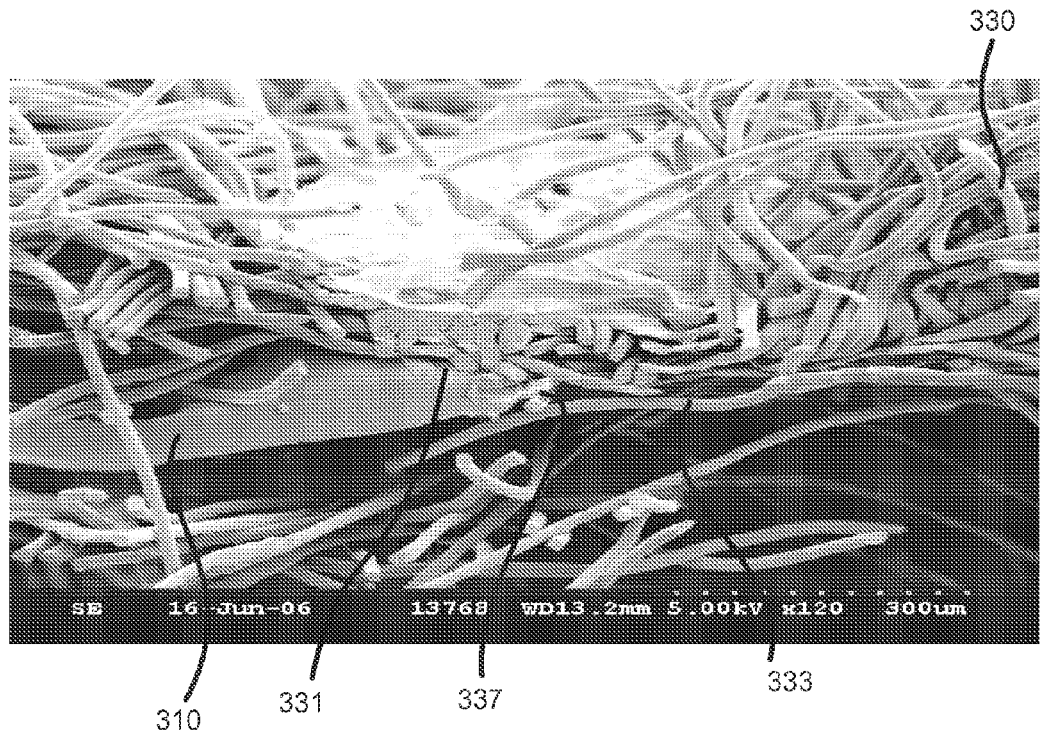
FIG. 13 is an SEM microphotograph (5 kv, 120×) of the sample formed in Example 1.
Figure 14:
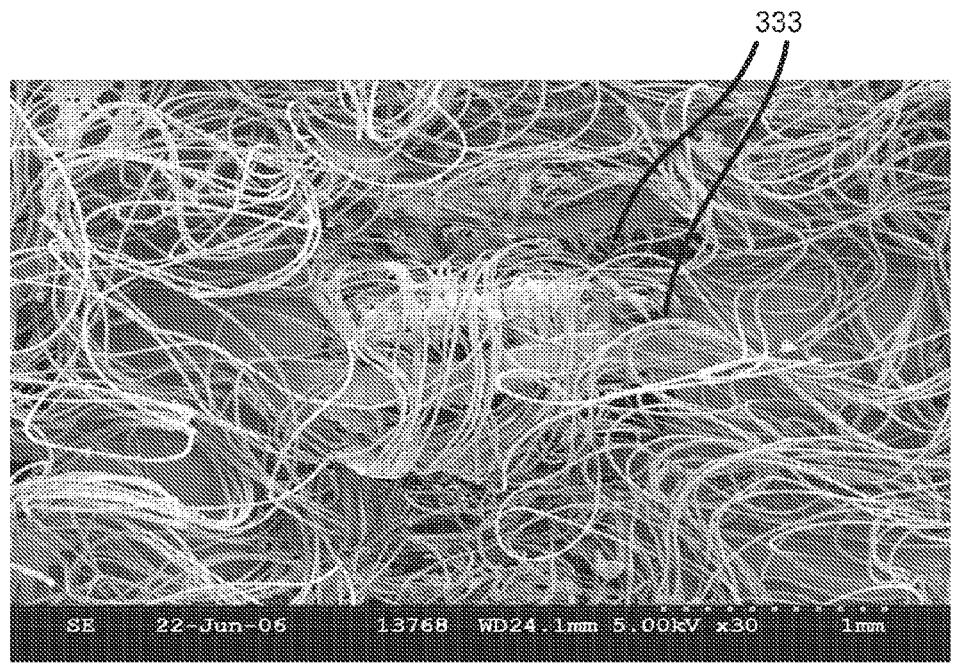
FIG. 14 is an SEM microphotograph (5 kv, 30×) of the sample formed in Example 1.
Figure 15:
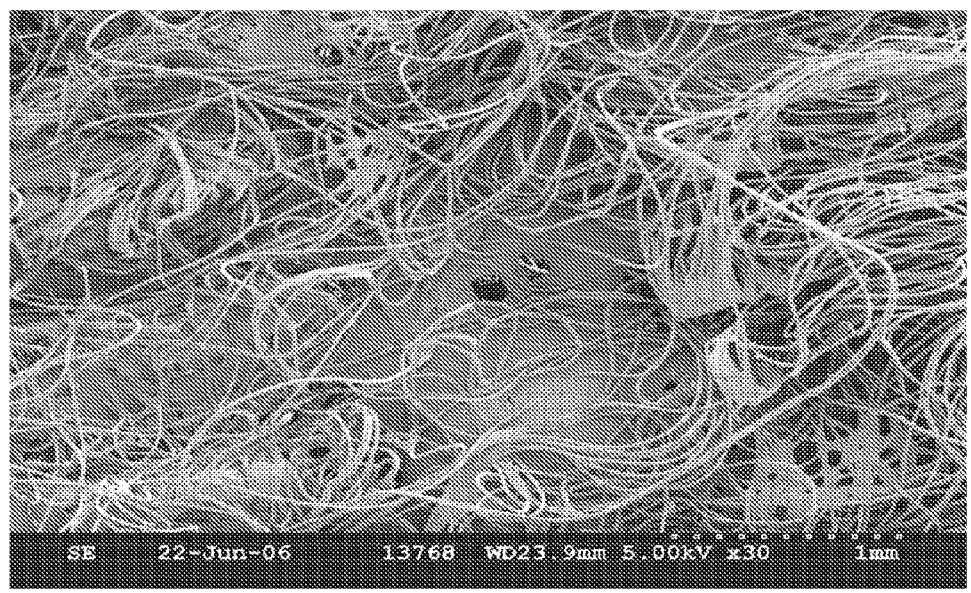
FIG. 15 is an SEM microphotograph (5 kv, 30×) of the sample formed in Example 1.
Figure 16:
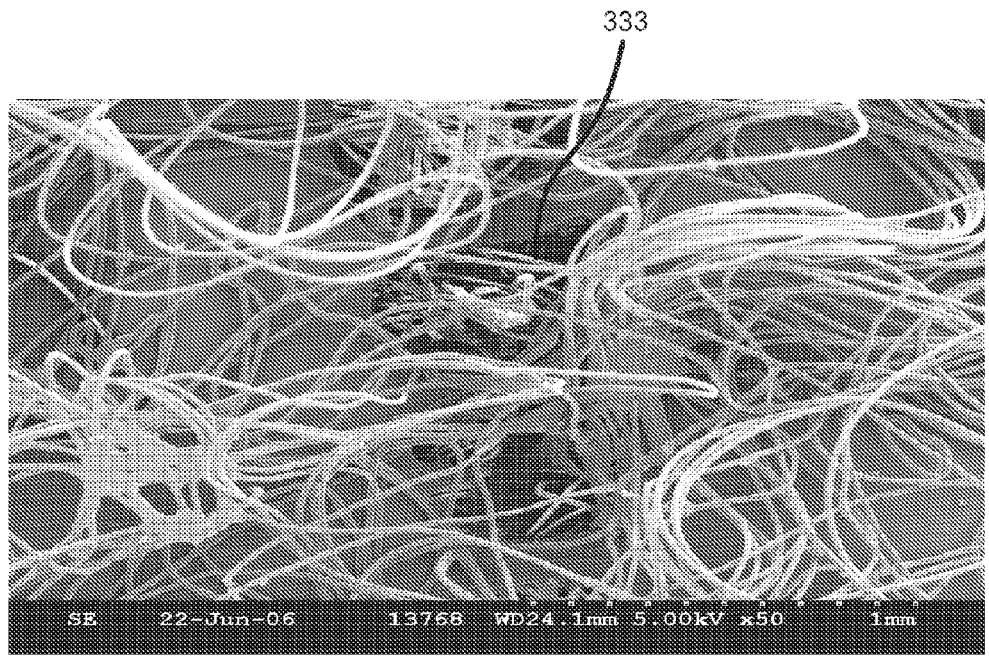
FIG. 16 is an SEM microphotograph (5 kv, 50×) of the sample formed in Example 1.
Figure 17:
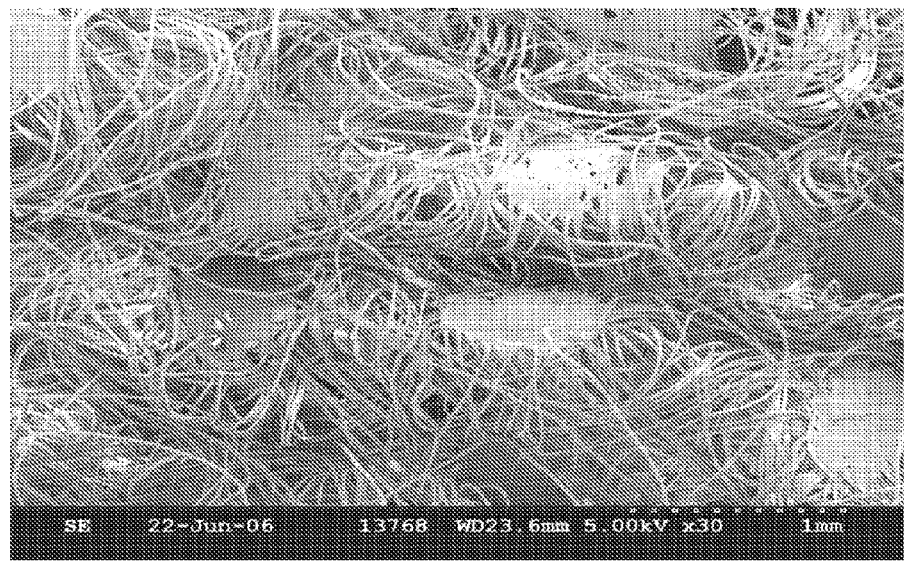
FIG. 17 is an SEM microphotograph (5 kv, 30×) of the sample formed in Example 1.

FIGS. 9-17 show scanning electron microphotographs of the resulting sample. FIG. 9, for instance, shows the approximately rectangular apertures 333*a* formed by the bars of the rib-knit pattern (See e.g., FIG. 3), while FIG. 10 shows the approximately circular apertures 333*b* formed by the pins of the rib-knit pattern. A perspective view of the apertures is shown in FIG. 11. The apertures 333 are also shown in FIGS. 14-17. In addition to illustrating apertures, the microphotographs also evidence the melt fusion of the elastic film to the fibers of the nonwoven webs. For instance, FIGS. 12-13 show an elastic film 310 that is melt fused to a nonwoven web 330 at discrete bond sites 331. The bond sites 331 are proximately located to a perimeter 337 defined by apertures 333.

EXAMPLE 2

The ability to form an elastic nonwoven composite was demonstrated. The elastic film was formed from 71 wt. % of EXACT™ 5361 (ExxonMobil Chemical Co.), 25 wt. % KRATON® MD6673 (Kraton Polymers, LLC of Houston Tex.), and 2 wt. % of a SCC116921 pigment (Standridge Color Corp.). KRATON® MD6673 contains 68 wt. % of a styrene-ethylene-butylene-styrene block copolymer (KRATON® MD6937), 20 wt. % REGALREZ™ 1126 (Eastman Chemical) and 12 wt. % EPOLENE™ C-10 polyethylene wax (Eastman Chemical). The SCC116921 pigment contained titanium dioxide blended with polypropylene and polypropylene random copolymers. The polymers were compounded by weighing appropriate portions of pellets of each polymer, combining them into one container, and mixing them together by stirring.

After compounding, the polymer composition was extruded at a melt temperature of 403° F. and cast onto a chill roll (set to a temperature of 21° C.) operating at a speed of about 45 feet per minute. The film was then thermally bonded between two polypropylene spunbond facings having a basis weight of approximately about 14 grams per square meter. Specifically, the film and facings were fed between an anvil and patterned roll (rib-knit). The patterned roll was heated to a roll surface temperature of 230° F., the anvil roll was heated to a roll surface temperature of 242° F., and the pressure was 176 pounds per linear inch. The rolls operated at a speed of 147 feet per minute so that the film was stretched in the machine direction at a stretch ratio of about 3.3 (i.e., 3.3 times its original length). Once formed, the composite was then introduced into a nip of intermeshing grooved steel rolls, such as shown in FIGS. 5-6, to stretch the composite in the cross machine direction. The grooved steel rolls were heated to a temperature of 125° F. Finally, the composite was transferred to a winder, which operated at a speed of 74 feet per minute to allow in the composite to retract. The final basis weight was approximately 100 grams per square meter.

EXAMPLE 3

The ability to form an elastic nonwoven composite was demonstrated. The elastic film was formed from 98 wt. % of EXACT™ 5361 (ExxonMobil Chemical Co.) and 2 wt. % of Dow Polyethylene 640I (Dow Chemical Co.). The polymers were compounded by weighing appropriate portions of pellets of each polymer, combining them into one container, and mixing them together by stirring. After compounding, the film samples were blown between a collapsing nip (operated at 30 feet per minute) so that a melt temperature of about 386° F. was achieved. The blown film was thermally bonded between two polypropylene spunbond facings having a basis weight of approximately about 17 grams per square meter. Specifically, the film and facings were fed between an anvil and patterned roll (S-weave). The patterned roll was heated to a roll surface temperature of 211° F., the anvil roll was heated to a roll surface temperature of 203° F., and the pressure was 117 pounds per linear inch. The rolls operated at a speed of 110 feet per minute so that the film was stretched in the machine direction at a stretch ratio of about 3.7 (i.e., 3.7 times its original length). Once formed, the composite was then transferred to a winder, which operated at a speed of 70 feet per minute to allow in the composite to retract. The final basis weight was approximately 88 grams per square meter.

EXAMPLE 4

The ability to form an elastic nonwoven composite was demonstrated. The elastic film was formed from 93 wt. % of VISTAMAXX™ 1100 (ExxonMobil Chemical Co.); 4 wt. % of Dow Polyethylene 640I (Dow Chemical Co.); and 3 wt. % of a SCC116921 pigment (Standridge Color Corp.). The SCC116921 pigment contained titanium dioxide blended with polypropylene and polypropylene random copolymers. The polymers were compounded by weighing appropriate portions of pellets of each polymer, combining them into one container, and mixing them together by stirring. After compounding, the film samples were blown between a collapsing nip (operated at 38 feet per minute) so that a melt temperature of about 390° F. was achieved. The blown film was thermally bonded between two polypropylene spunbond facings having a basis weight of approximately about 14 grams per square meter. Specifically, the film and facings were fed between an anvil and patterned roll (rib-knit). The patterned roll was heated to a roll surface temperature of 193° F., the anvil roll was heated to a roll surface temperature of 203° F., and the pressure was 117 pounds per linear inch. The rolls operated at a speed of 210 feet per minute so that the film was stretched in the machine direction at a stretch ratio of about 5.5 (i.e., 5.5 times its original length). Once formed, the composite was then introduced into a nip of intermeshing grooved steel rolls, such as shown in FIGS. 5-6, to stretch the composite in the cross machine direction. The grooved steel rolls were heated to a temperature of 125° F. Finally, the composite was transferred to a winder, which operated at a speed of 79 feet per minute to allow in the composite to retract. The final basis weight was approximately 98 grams per square meter.

EXAMPLE 5

The elasticity (e.g., cycle testing), air permeability, peel strength, and strain of the composites of Examples 1-4 were tested. The results are set forth below in Tables 1 and 2.

TABLE 1

Cycle Testing of the Samples

| | Cycle 1 | | | | | | | | | | | |
|---|---|---|---|---|---|---|---|---|---|---|---|---|
| Example | Up 50% ($g_f$) | Up 75% ($g_f$) | Up 100% ($g_f$) | Up 125% ($g_f$) | Up 150% ($g_f$) | Down 50% ($g_f$) | Down 75% ($g_f$) | Down 100% ($g_f$) | Down 125% ($g_f$) | Down 150% ($g_f$) | Hyst. Loss (%) | Imm. Set (%) |
| 1 | 452 | 617 | 800 | 1129 | 2473 | 63 | 141 | 241 | 421 | 1641 | 67.5 | 31.4 |
| 2 | 385 | — | — | — | — | — | — | — | — | — | — | — |
| 3 | 846 | — | — | — | — | — | — | — | — | — | — | — |
| 4 | 669 | 921 | 1136 | 1388 | 1720 | 148 | 243 | 359 | 572 | 1407 | 62.9 | 17.1 |

TABLE 2

Porosity and Mechanical Properties of the Samples

| Ex. | Air Permeability (ft³/min) | MD Peel Strength ($g_f$/inch) | Strain at 200 $g_f$ (%) |
|---|---|---|---|
| 1 | 190.0 | 31.8 | 148 |
| 2 | 181.7 | — | 115 |
| 3 | 243.3 | — | 56 |
| 4 | 9.0 | 73.0 | 156 |

As indicated above, the composites of the present invention exhibited elastic characteristics, while also maintaining good air flow and mechanical properties.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of forming a nonwoven composite, the method comprising:
   forming an elastic film from an elastomeric polymer;
   passing the film and a nonwoven web material that contains fibers through a nip formed by at least one roll patterned with raised bonding elements; and
   at the nip, concurrently forming apertures in the film and melt fusing the film to the nonwoven web material so that the elastomeric polymer physically adheres to the fibers at a plurality of corresponding discrete bond sites, thus forming one or more discrete bond sites between the film and the nonwoven web material located proximate to a perimeter defined by at least one of the apertures, wherein at least one aperture has a length of from about 200 to about 5000 micrometers, and wherein the nonwoven web material remains generally unapertured at an area adjacent to the aperture in the film and remains generally unbonded to the film except at the corresponding discrete bond sites after being melt fused to the film.

2. The method of claim 1, wherein the nip is formed between two rolls.

3. The method of claim 1, wherein the film is under tension at a stretch ratio of from about 2.5 to about 7.0 at the nip.

4. The method of claim 3, wherein the stretch ratio is from about 3.0 to about 5.5.

5. The method of claim 1, wherein the elastic film is stretched prior to passing through the nip.

6. The method of claim 1, wherein the elastic film under tension in the machine direction.

7. The method of claim 1, wherein the elastic film is under tension in the cross-machine direction.

8. The method of claim 1, wherein at least one of the rolls is heated to a temperature of from about 50° C. to about 160° C.

9. The method of claim 1, wherein at least one of the rolls is heated to a surface temperature of from about 70° C. to about 120° C.

10. The method of claim 1, wherein at least one of the bonding elements is oriented from about 30° to about 150° relative to the machine direction.

11. The method of claim 1, wherein at least one of the bonding elements is oriented from about 45° to about 135° relative to the machine direction.

12. The method of claim 1, wherein a pressure of from about 75 to about 600 pounds per linear inch is applied at the nip.

13. The method of claim 1, wherein a pressure of from about 120 to about 200 pounds per linear inch is applied at the nip.

14. The method of claim 1, further comprising allowing the composite to retract in the machine direction prior to or during winding onto a roll.

15. The method of claim 1, further comprising mechanically stretching the composite in at least the cross-machine direction.

16. The method of claim 1, wherein the elastomeric polymer comprises an elastomeric, single-site catalyzed semi-crystalline polyolefin.

17. The method of claim 16, wherein the single-site catalyzed polyolefin includes an ethylene/α-olefin copolymer, propylene/α-olefin copolymer, or a combination thereof.

18. The method of claim 1, wherein the elastomeric polymer comprises an elastomeric block copolymer.

19. The method of claim 1, wherein the nonwoven web material is substantially unapertured after being melt fused to the film.

20. The method of claim 1, wherein at an area adjacent to the aperture in the film, the nonwoven web material is free from apertures having a length of from about 200 to about 5000 micrometers.

21. The method of claim 1, wherein the nonwoven web material is free from apertures having a length of from about 200 to about 5000 micrometers.

22. The method of claim 1, wherein an additional nonwoven web material is passed through the nip so that the elastic film is positioned between the nonwoven web materials.

23. The method of claim 1, wherein the composite is liquid permeable.

24. The method of claim 1, wherein the nonwoven web material contains spunbond fibers, meltblown fibers, staple fibers, or a combination thereof.

25. The method of claim 1, wherein the nonwoven web material is a polyolefin.

26. The method of claim 25, wherein the polyolefin is polypropylene.

27. The method of claim 1, wherein the nonwoven web material contains a polymer having a Vicat softening point of from about 130'C to about 200° C.

28. The method of claim 1, wherein at least one of the apertures has a length of from about 350 to about 4000 micrometers.

* * * * *